United States Patent [19]

Kamachi et al.

[11] Patent Number: 5,227,370
[45] Date of Patent: Jul. 13, 1993

[54] PRADIMICIN DERIVATIVES

[75] Inventors: Hajime Kamachi, Urayasu; Seiji Iimura, Tokyo; Satsuki Okuyama, Hachioji; Shimpei Aburaki; Takayuki Naito, both of Kawasaki, all of Japan; Yasutsugu Ueda, Clinton, Conn.; Leonard B. Crast, Jr., Durham, Conn.; Amarendra B. Mikkilineni, Middletown, Conn.

[73] Assignee: Bristol-Myers Squibb Company, New York, N.Y.

[21] Appl. No.: 802,020

[22] Filed: Dec. 3, 1991

Related U.S. Application Data

[63] Continuation of Ser. No. 436,505, Nov. 14, 1989, abandoned.

[51] Int. Cl.$^5$ .................. A61K 31/70; C07H 15/24
[52] U.S. Cl. ........................... 514/27; 514/33; 536/6.4; 536/17.2; 536/18.1
[58] Field of Search ............ 514/27, 33; 536/6.4, 536/17.2, 18.1

[56] References Cited

U.S. PATENT DOCUMENTS

| | | | |
|---|---|---|---|
| 4,870,165 | 9/1989 | Oki et al. | 536/6.4 |
| 4,960,755 | 10/1990 | Nishio et al. | 514/8 |
| 4,973,673 | 11/1990 | Sawada et al. | 536/6.4 |
| 4,992,425 | 2/1991 | Nishio et al. | 514/33 |

FOREIGN PATENT DOCUMENTS 315147 5/1989 European Pat. Off. .
378126 7/1990 European Pat. Off. .

OTHER PUBLICATIONS

Abstract of 27th Interscience Conference on Antimicrobial Agents and Chemotherapy (Oct. 4,–Jul. 1987, New York, NY) p. 268, Abst. No. 984.
J. Antibiot., 1988, 41 (6):807–811.
J. Antibiot., 1988, 41 (8):1019–1028.

Primary Examiner—Johnnie R. Brown
Assistant Examiner—Elli Peselev
Attorney, Agent, or Firm—Mollie M. Yang

[57] ABSTRACT

The present invention provides pradimicin analogs which exhibit improved water solubility relative to parent compounds. These novel agents are useful in treatment of fungal infections.

13 Claims, No Drawings

PRADIMICIN DERIVATIVES

CROSS REFERENCE TO RELATED APPLICATION

This application is a continuation of our co-pending application Ser. No. 07/436,505 filed Nov. 14, 1989, now abandoned.

BACKGROUND OF THE INVENTION

1. Field of the Invention

The present invention relates to semi-synthetic antifungal compounds, their therapeutic use and pharmaceutical compositions containing them. More particularly, these antifungal compounds are derivatives of pradimicins.

2. Information Disclosure Statement

Pradimicins, also known as BU-3608 antibiotics, are a group of antifungal antibiotics produced by *Actinomadura hibisca* sp. nov. Various pradimicins that have been isolated from fermentation broths of *Actinomadura hibisca* or variants or mutants thereof, and their structures, are depicted below:

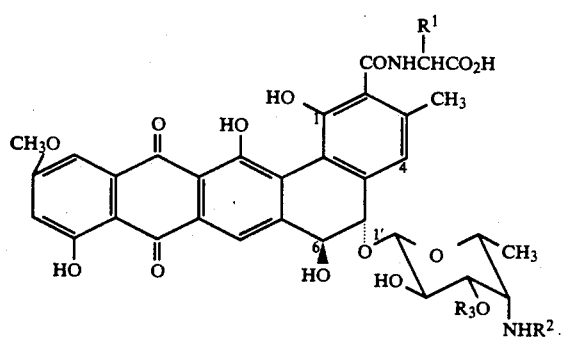

(a) Pradimicin A:   $R^1 = CH_3$; $R^2 = CH_3$; $R^3 = \beta$-D-xylosyl
(b) Pradimicin B:   $R^1 = CH_3$; $R^2 = CH_3$; $R^3 = H$
(c) Pradimicin C:   $R^1 = CH_3$; $R^2 = H$; $R^3 = \beta$-D-xyloxyl
(d) Pradimicin D:   $R^1 = H$; $R^2 = CH_3$; $R^3 = \beta$-D-xylosyl
(e) Pradimicin E:   $R^1 = H$; $R^2 = H$; $R^3 = \beta$-D-xylosyl
(f) Pradimicin FA-1: $R^1 = CH_2OH$; $R^2 = CH_3$; $R^3 = \beta$-D-xylosyl
(g) Pradimicin FA-2: $R^1 = CH_2OH$; $R^2 = H$; $R^3 = \beta$-D-xylosyl Pradimicin A was reported as BMY-28567 in Abstract No. 984 of the 27th Interscience Conference on Antimicrobial Agents and Chemotherapy, Oct. 4–7, 1987, New York, N.Y. Pradimicins A, B, and C are disclosed in European Patent Application No. 277,621. Pradimicins D, E and their respective desxylosyl derivatives are disclosed in our co-pending application, U.S. Ser. No. 203,776, filed Jun. 7, 1988, now U.S. Pat. No. 4,992,245.

N-alkylated analogs of pradimicins A, B, C, D, E and their desxylosyl derivatives are disclosed in our co-pending application U.S. Ser. No. 221,144 filed Jul. 19, 1988, now U.S. Pat. No. 4,960,755.

Pradimicins FA-1, FA-2, their respective desxylosyl derivatives, and their N-alkylated analogs are disclosed in our co-pending application, U.S. Ser. No. 269,821, filed Nov. 10, 1988, now U.S. Pat. No. 4,973,673.

Two compounds, known as benanomicins A and B, were reported in *J. Antibiot.*, 1988, 41 (6):807–811, and ibid, 41 (8):1019–1028. Benanomicin B appears to be identical to pradimicin C, whereas benanomicin A has a hydroxyl group in place of the sugar amino group of benanomicin B.

SUMMARY OF THE INVENTION

The present invention provides a compound of formula (II)

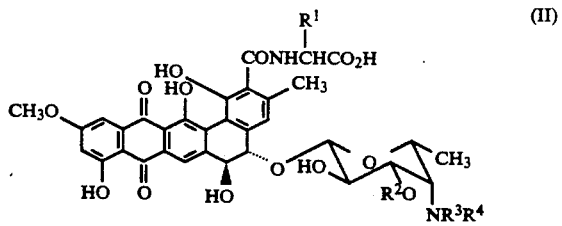

wherein $R^1$ is selected from the group consisting of H, methyl, and hydroxymethyl, and when $R^1$ is methyl or hydroxymethyl, the resulting amino acid has the D-configuration; $R^2$ is H or $\beta$-D-xylosyl; $R^3$ is H or methyl; and $R^4$ is selected from the group consisting of ($C_{2-5}$)alkenyl; ($C_{2-5}$)alkynyl; substituted ($C_{1-5}$) alkyl; substituted ($C_{2-5}$) alkenyl; wherein the substituent for both the alkyl and alkenyl is a group selected from the group consisting of carboxy, ($C_{1-5}$)alkoxycarbonyl, carbamyl, ($C_{1-5}$)alkylcarbamyl, di($C_{1-5}$)alkylcarbamyl, and sulfonyl; ($C_{1-5}$)alkanoyl substituted with a group selected from the group consisting of amino, ($C_{1-5}$)alkylamino, and di($C_{1-5}$)alkylamino; L-glutamyl; formyl; benzyl; and p-tolysulfonylcarbamyl; or a pharmaceutically acceptable salt thereof.

A further aspect of the present invention provides a method for treating fungal infections in a mammalian host in need of such treatment which comprises administering to said host an antifungal effective dose of a compound of formula (II).

Yet a further aspect of the present invention provides a pharmaceutical composition which comprises a compound of formula (II) and a pharmaceutically acceptable carrier.

Compounds of the present invention exhibit higher water solubility than parent compound pradimicins A and B.

DETAILED DESCRIPTION OF THE INVENTION

The present invention provides as a preferred embodiment compounds of formula (II) wherein $R^4$ is ($C_{1-5}$)alkanoyl substituted with a group selected from the group consisting of amino, ($C_{1-5}$)alkylamino, and di($C_{1-5}$)alkylamino. A more preferred embodiment provides compounds of formula (II) wherein $R^4$ is ($C_{2-3}$) alkanoyl substituted with a group selected from the group consisting of amino, ($C_{1-5}$)alkylamino, and di($C_{1-5}$)alkylamino, with the amino group being the most preferred substituent.

A further preferred embodiment provides compounds of formula (II) wherein $R^4$ is ($C_{1-5}$)alkyl substituted with a group selected from the group consisting of carboxy, carbamyl, ($C_{1-5}$)alkoxycarbonyl, and sulfonyl; ($C_{3-5}$)alkenyl; ($C_{3-5}$)alkynyl; or ($C_{3-5}$)alkenyl substituted with a group selected from carboxy and ($C_{1-5}$)alkoxycarbonyl.

As used in the specification and claims, unless indicated otherwise, "alkyl" includes straight and branched carbon chains. "Pharmaceutically acceptable salt" may be an internal salt; an organic or inorganic base salt, such as the sodium, potassium, lithium, ammonium, and trialkylammonium salt; or an acid addition salt with a mineral acid or an organic acid, e.g. the hydrochloride, sulfate, hydrogen sulfate, phosphate, formate, and acetate salt. An amino substituted $(C_{1-5})$alkanoyl includes the carbamyl radical; similarly, a mono- or dialkylamino substituted $(C_{1-5})$alkanoyl includes the correspondingly substituted carbamyl radical. "Pradimicin" refers to a member of the naturally occurring pradimicins, their desxylosyl derivatives, and their respective salts.

The pradimicin starting materials and methods for their production are disclosed in our co-pending applications U.S. Ser. No. 115,273, filed Nov. 2, 1987, now U.S. Pat. No. 4,870,165, U.S. Ser. No. 203,776, filed Jun. 7, 1988, now U.S. Pat. No. 4,992,245, U.S. Ser. No. 221,144, filed Jul. 19, 1988, now U.S. Pat. No. 4,960,755, and U.S. Ser. No. 269,821, filed Nov. 10, 1988, now U.S. Pat. No. 4,973,673. The disclosures contained in these applications are hereby incorporated by reference. The pradimicins may be used as the free base, acid or base addition salts, the zwitterion, or esters of the carboxylic group, depending on the particular reaction conditions. Base salts may be e.g. sodium, potassium, lithium, calcium, magnesium, ammonium, and trialkylammonium salts; acid addition salts may be e.g. hydrochloride, sulfate, nitrate, and the like. Carboxylic acid ester may be a lower alkyl ester such as methyl, ethyl and isopropyl; phenyl, benzyl, or a cycloalkyl e.g. cyclohexyl ester.

Compounds of the present invention may be prepared by methods well known in the art. Thus, substituted alkyl or alkenyl group may be introduced by direct nucleophilic displacement or by reductive alkylation involving the sugar amino group; N-acyl derivatives may be prepared by reacting the sugar amino group with the desired acid or an acylating equivalent thereof. Each of the reactions mentioned above will now be discussed in detail herein below.

N-(substituted alkyl) derivatives of pradimicins may be prepared by reacting a pradimicin with a compound generally represented as L-A wherein L is a leaving group, such as chloride, bromide, or iodide, and A is substituted $(C_{1-5})$alkyl or $(C_{2-5})$alkenyl where the substituents are as previously defined under formula (II). Example of L-As include, but are not limited to, iodoacetic acid, iodopropionic acid, iodoacetamide, ethyl iodoacetate, and methyl bromocrotonate. The reaction is carried out in an inert organic solvent such as methylene chloride, or in water, or in a mixture thereof. The choice of solvent depends on the nature of the reactants. The reaction temperature is not critical and may be any that facilitates product formation in a reasonable time. The temperature may range from about room temperature to the refluxing temperature of the reaction solution, and the reaction time may be from about 30 minutes to about 15 hours, depending on the reactants and the reaction milieu. In carrying out the alkylation reaction, it may be advantageous to block the hydroxyl and phenol groups of pradimicin. Although not particularly restricted, the blocking group is preferably the trimethylsilyl (TMS) group which may be introduced using N,O-bis(trimethylsilyl)acetamide (BSA). The molar amount of BSA employed is at least equivalent to the number of OH groups to be blocked but preferably it is used in excess at about 1.2 to about 3 times that number. Upon completion of the alkylation reaction, the TMS group may be removed by acid hydrolysis or by using a reagent such as tetrabutylammonium fluoride.

Alternatively, N-(substituted alkyl) derivatives of pradimicin may be prepared by reductive alkylation which comprises first condensing the pradimicin starting material with an appropriate compound containing an aldehyde or a ketone functionality followed by treatment of the product thus formed with a reducing agent. The aldehyde or ketone may be, for example, glyoxylic acid, pyruvic acid, acetoactic acid, and ethyl acetoacetate. The reducing agent may be, for example, a metal hydride such as sodium borohydride, sodiumcyanoborohydride, and lithium aluminum hydride; sodium cyanoborohydride is the preferred reagent. The condensation reaction is carried out in an inert organic solvent such as acetonitrile, lower alkanol, dimethyl sulfoxide, or a mixture thereof, or an aqueous solution thereof. The reaction temperature is not particularly restricted and may be from room temperature to the refluxing temperature of the reaction mixture. The reaction time may range from several minutes to a few hours. The condensation product formed may then be reduced in the same reaction vessel. The reduction may be carried out at room temperature until the desired product is obtained. In our experience, reductive alkylation at room temperature of pradimicin B with glyoxylic acid and using sodium cyanoborohydride as the reducing agent is complete within several hours. Optimum reaction conditions will, of course, depend on the nature and reactivity of the particular reactants used.

N-acylated pradimicins of the present invention may be prepared by reacting a pradimicin with an amino acid, an N-alkyl or N,N-dialkyl amino acid, or an acylating equivalent thereof. The amino acid may be, for example, glycine, $\beta$-amino alanine, N,N-dimethyl glycine, and the like. Acylating equivalents derived from the acid may be, for example, an acid halide such as acid chloride, active ester derived from N-hydroxysuccinimide or 1-hydroxybenzotriazole, and symmetrical or mixed anhydride. When the carboxylic acid is used as the acylating species, it is preferably used in conjunction with a condensing agent, for example, a carbodiimide such as dicyclohexylcarbodiimide (DCC). The amino group on the acid reactant is preferably protected. The protecting group for the amino group is not particularly restricted and may be one commonly used in the art of peptide synthesis. The choice of protecting groups, as well methods for protection and deprotection, is discussed in, e.g. chapter 4 of "Peptide Synthesis", 2Ed., by Bodanszky, et al. We have found the t-butoxycarbonyl (t-BOC) group, which is removable under acidic conditions, e.g. using trifluoroacetic acid, to be satisfactory for the present invention. The acylaton reaction may be carried out in an inert organic solvent, such as dimethylformamide, methylene chloride, and dichloroethane. The reaction mixture may optionally include an acid acceptor when acid is expected to be a by-product; suitable acid acceptors are, for example, tertiary amine bases such as pyridine, triethylamine, diisopropylethylamine, and the like, or inorganic bases such as sodium and potassium carbonates. The reaction temperature may be from room temperature to the refluxing temperature of the reaction mixture, and the reaction may be from about 30 minutes to several days; these parameters are not critical and may be adjusted depending on the nature of the reactants to maximize product yield. The hydroxyl and phenol groups of the pradimicin starting material may be either unprotected or blocked. A preferred blocking group for the OH groups is the TMS, as previously discussed. When the unprotected pradimicin is used, the OH groups may also become acylated to form esters. The esters thus formed may be hydrolyzed under basic conditions without cleaving the newly formed amide linkage.

N-carbamyl derivatives of pradimicin may be obtained by reacting a pradimicin and an appropriate isocyanate. The reaction is carried out in an inert organic solvent, such as acetonitrile, and at room temperature. The reaction time may range from an hour to several days.

As previously mentioned, pradimicins may be used as the free base, a base salt, an acid addition salt, or an ester of the carboxylic acid. If an ester is used, the ester group may be removed by alkaline hydrolysis to generate the final product.

It is to be understood that synthesis of compounds of the present invention is not limited to the procedures and reagents outlined above, but may include other methods capable of alkylating or acylating the amino group on the sugar portion of pradimicins. The reaction conditions will, of course, vary with the choice of starting materials but may be readily ascertained by a skilled artisan without undue experimentation.

BIOLOGICAL ACTIVITY

In vitro antifungal activity of representative compounds of the present invention was determined against different fungi by the serial agar dilution method. The inoculum size was adjusted to $10^6$ cells/ml, and a volume of approximately 0.003 ml of fungal suspension was applied to the surface of the antibiotic containing agar plates with a multiinoculator. After incubation, the lowest concentration of antibiotic causing virtually complete inhibition of fungal growth was determined as the minimum inhibitory concentration (MIC). The results are summarized in Tables 1 and 1a.

TABLE 1

In Vitro Antifungal Activity*

| Test Organism | Pradimicin A | Ex. 1 | Ex. 2 | Ex. 3 | Ex. 7 | Ex. 8** | Ex. 9 | Ex. 10 | Ex. 11 | Ex. 12 | Ex. 13 | Ex. 16 |
|---|---|---|---|---|---|---|---|---|---|---|---|---|
| Candida albicans IAM4888 | 6.3 | 50.0 | 25.0 | 25.0 | 3.1 | 3.1 | 25.0 | 6.3 | 12.5 (6.3) | 25.0 | 50.0 | 6.3 |
| Candida albincans A9540 | 50.0 | 50.0 | 50.0 | 50.0 | 3.1 | 6.3 | 25.0 | 12.5 | 12.5 (6.3) | >25.0 | 100.0 | 6.3 |
| Cryptococcus neoformans D49 | 0.8 | 25.0 | 12.5 | 6.3 | 0.4 | 0.8 | 25.0 | 1.6 | 1.6 | 6.3 | 50.0 | 3.4 |
| Cryptococcus neoformans IAM4514 | 0.8 | 12.5 | 3.1 | 6.3 | 0.4 | 0.8 | 12.5 | 1.6 | 1.6 | 6.3 | 25.0 | 3.1 |
| Aspergillus fumigatus IAM2530 | 3.1 | 100.0 | 12.5 | 50.0 (25.0) | 3.1 | 1.6 | 50.0 | 12.5 | 50.0 | 12.5 | 100.0 | 12.5 |
| Aspergillus fumigatus IAM2034 | 3.1 | >100.0 (50.0) | >100.0 (50.0) | >100.0 (100.0) | >50.0 | 3.1 | 50.0 | 100.0 | 100.0 | 12.5 | 100.0 | 12.5 |
| Asoergukkys flavus FA21436 | 6.3 | >100.0 | >100.0 (50.0) | >100.0 (50.0) | >50.0 (3.1) | 6.3 | >100.0 | >100.0 | >100.0 (100.0) | 25.0 | 100.0 | >50.0 |
| Fusarium moniliforme A2284 | 3.1 | >100.0 | >100.0 | >100.0 | >50.0 | 3.1 | >100.0 | >100.0 | >100.0 | >25.0 | >100.0 | >50.0 |
| Trichophyton mentagrophytes D155 | 6.3 | >100.0 | >100.0 | >100.0 | 50.0 | 6.3 | 25.0 | 12.5 | 100.0 | 12.5 | >100.0 | 6.3 |
| Trichophyton mentagrophytes #4329 | 3.1 | >100.0 | >100.0 | >100.0 | 25.0 | 3.1 | 25.0 | 12.5 | 100.0 | 25.0 | >100.0 | 6.3 |
| Blastomyces dermatidis D40 | 3.1 | >100.0 (50.0) | 25.0 (12.5) | 100.0 (12.5) | 3.1 | 1.6 | 100.0 | 12.5 | 12.5 | >25.0 | >100.0 | 50.0 |
| Sprotricosis schenckii IF08158 | 1.6 | >100.0 (50.0) | 25.0 (12.5) | 25.0 (12.5) | 1.6 | 1.6 | 50.0 | 12.5 | 6.3 | 12.5 | 100.0 | 6.3 |
| Petyriellidium boydii IF08078 | 12.5 | >100.0 | >100.0 | >100.0 | >50.0 | 6.3 | ND | ND | >100.0 | >25.0 | >100.0 | >50.0 |
| Mucor spinosus IF05317 | >100.0 (12.5) | >100.0 (100.0) | >100.0 (100.0) | >100.0 (100.0) | >50.0 | >50.0 (6.3) | >100.0 (50.0) | >100.0 | >100.0 (25.0) | >25.0 | >100.0 | >50.0 |

( ): Partial Inhibition;
ND: Not Determined
*Media: Sabouraud dextrose agar (pH 7.0);
Incubation Condition: 28° C. for 40 hours.
**A 1:3 mixture of compound of Example 8 and pradimicin A.

TABLE 1a

In Vitro Antifungal Activity*

| MICs (μg/mL) Organisms | Pradimicin A | Pradimicin B | Ex. 4 | Ex. 5 | Ex. 6 | Ex. 14 | Ex. 15 | Ex. 17 | Ex. 18 | Ex. 19 | Ex. 20 | Ex. 21 | Ex. 22 | Ex. 23 | Ex. 24 |
|---|---|---|---|---|---|---|---|---|---|---|---|---|---|---|---|
| Candida albicans A9540 | >50 | 3.2 | 3.2 | 3.2 | 6.3 | 3.2 | 6.3 | 6.3 | 25 | 12.5 | 25 | 3.2 | >50 | 50 | >50 |
| Candida albicans A25578 | 3.2 | 1.6 | 1.6 | 0.8 | 3.2 | 3.2 | 3.2 | 3.2 | 25 | 12.5 | 12.5 | 0.8 | 3.2 | 1.6 | >50 |
| Candida tropicalis A25809 | 1.6 | 0.8 | 1.6 | 0.8 | 1.6 | 3.2 | 3.2 | 1.6 | ND | 6.3 | ND | 1.6 | ND | 1.6 | ND |
| Candida tropicalis A25812 | >50 | 3.2 | 3.2 | 3.2 | 3.2 | 3.2 | 6.3 | 6.3 | 25 | 12.5 | 25 | 6.3 | >50 | 50 | >50 |
| Candida | 3.2 | 0.8 | 1.6 | 0.8 | 1.6 | 1.6 | 1.6 | 1.6 | 3.2 | 3.2 | 6.3 | 0.8 | 3.2 | 1.6 | 12.5 |

TABLE 1a-continued

| MICs (μg/mL) Organisms | Pradimicin A | Pradimicin B | Ex. 4 | Ex. 5 | Ex. 6 | Ex. 14 | Ex. 15 | Ex. 17 | Ex. 18 | Ex. 19 | Ex. 20 | Ex. 21 | Ex. 22 | Ex. 23 | Ex. 24 |
|---|---|---|---|---|---|---|---|---|---|---|---|---|---|---|---|
| *pseudotropicalis* A25802 | | | | | | | | | | | | | | | |
| *Candida paratropicalis* A25825 | >50 | 3.2 | 3.2 | 3.2 | 6.3 | 3.2 | 6.3 | 6.3 | 25 | 25 | 25 | 6.3 | >50 | >50 | >50 |
| *Saccharomyces cerevisiae* A25803 | 0.8 | 0.8 | 0.8 | 0.8 | 0.8 | 1.6 | 3.2 | 1.6 | ND | 3.2 | 6.3 | 0.8 | ND | 0.8 | ND |
| *Cryptococcus neoformans* A15053 | 0.4 | 0.8 | 1.6 | 0.8 | 1.6 | 1.6 | 3.2 | 6.3 | >50 | 6.3 | 50 | 1.6 | 0.4 | 1.6 | 1.6 |
| *Microsporum gypseum* WW1107 | 12.5 | 12.5 | 25 | 3.2 | 12.5 | 3.2**[1] | 12.5 | 25 | >50**[4] | 50 | 12.5**[1] | 12.5 | >50 | >50 | >50**[4] |
| *Microsporum canis* WW10218 | 1.6 | 3.2 | 6.3 | 1.6 | 1.6 | ND | 6.4 | 25 | >50**[5] | 12.5 | 12.5**[6] | 3.2 | 1.6 | 25 | 25**[5] |
| *Trichophyton rubrum* A26761 | 6.3 | 3.2 | 12.5 | 1.6 | 6.3 | 1.6**[2] | 2.5 | 25 | >50 | 50 | 12.5**[2] | 3.2 | ND | 25 | 3.2 |
| *Trichophyton mentagrophytes* A26771 | 6.3 | 3.2 | 12.5 | 1.6 | 6.3 | 1.6**[3] | 12.5 | 25 | >50 | 50 | 12.5**[3] | 3.2 | >50 | 25 | 3.2 |

ND = Not Determined
*Media = YM agar (pH 7.0, Difco);
incubation conditions: 30° C. for 2 days (yeast) or 4 days (filamentous fungi).
**The strains of organism used are:
1, *M. gypseum* A22810;
2, *T. rubrum* A24195;
3, *T. mentagrophytes* A22838;
4, *M. gypseum* A26835;
5, *M. canis* A26834;
6, *M. canis* A22494.

Several compounds were also evaluated in an intravenous *Candida albicans* A95040 infection mouse model. died between 7 to 15 days. The in vivo test results are summarized in Table 2.

TABLE 2

In vivo Antifungal Activity Against *Candida albicans* A9540 in Mice

| A. Compound | $PD_{50}$* (mg/kg, IV) | B. Compound | $PD_{50}$* (mg/kg) | Route |
|---|---|---|---|---|
| Ex. 1 | 45 | Ex. 4 | >50** | IV |
| Ex. 2 | 29 | Ex. 5 | >50** | IV |
| Ex. 3 | 18 | Ex. 21 | >50 | IV |
| Ex. 7 | 7.2 | Ex. 23 | >50 | IV |
| Ex. 9 | >50 | Pradimicin A | 30 | IV |
| Pradimicin A | 7.9 | Pradimicin B | 32 | IV |
| Ex. 10 | 30 | Ex. 4 | >50** | IM |
| Ex. 11 | 36 | Pradimicin A | 8.2 | IM |
| Pradimicin A | 11 | Pradimicin B | >50 | IM |

*Det'd 20 days after fungal challenge according to method of Litchfield and Wilcoxon.
1) Test organisms cultured @ 28° C. for 18 hrs in YGP medium (yeast extract, glucose, peptone, $K_2HPO_4$, $MgSO_4$, pH 6.6)
2) Drug administered once IV just after infection.

*Det'd 21 days after fungal challenge according to method of Spearman-Karber.
**delayed death observed.
1) Test organisms incubated for 18 hrs on Sabouraud dextrose agar.
2) Drug administered IM or IV at 1 and 3.5 hrs after infection and twice on the following day.

The test organism was suspended in saline approximately 10 times the median lethal dose of the fungus ($10^6$ cells/mouse) were used to infect intravenously male ICR mice weighing 20 to 24 g. Groups of five mice at each dose level were given the test compounds intravenously or intramuscularly. The 50% protective dose ($PD_{50}$) was calculated from survival rates recorded 20 or 21 days after the fungal challenge. Control animals Water Solubility The water solubility of representative compounds of the present invention was determined using one of the following protocols:

I. The sample (1.0 mg or 2.5 mg) was suspended in 250 μL of Dulbecco's phosphate buffer saline (PBS, without CaCl₂ and MgCl₂·6H₂O), sonicated at room temperature for 10 minutes, and centrifuged for 10 minutes. The supernatant (2 μL) was analyzed by HPLC using the conditions specified for each compound in the Experimental Section. When visibly soluble, the solubility was determined as >4 mg/mL (or >10 mg/ml for 2.5 mg sample used). When not soluble, an additional amount of PBS (X μL) was added, sonicated, and centrifuged. When visibly soluble, the solution (2 μL) was injected to HPLC and the peak area was used for the known concentration of the sample. Comparing the peak area obtained in the previous supernatant, the solubility was calculated as follows:

$$\text{solubility} = \frac{A}{A_o} \times \frac{8}{x} \text{ mg/ml}$$

where A is the peak area of the supernatant of 1.0 mg sample in 250 μL PBS and Ao is the peak area of the complete solution of 1.0 mg sample in X μL, PBS.

II. The sample (3~3.5 mg) was suspended in 1 ml of PBS(−) or PBS(+), sonicated at 30° C. for 10 minutes, and allowed to stand at room temperature for 2 hours. The resulting solution or suspension was centrifuged at 12,000 rpm for 10 minutes. The supernatant (pH 6.7~7.2) was diluted (5× or 50×) with 0.01N NaOH (pH ca. 11.5) and its UV absorption at 500 nm was measured. The solubility was assessed by the absorption coefficient value with reference to the standard. Standard: Pure pradimicin A=E$_{1cm}$¹% 180 at 500 nm in alkaline solution. The zwitterionic form sample was used for the solubility test as it is. The hydrochloride salt sample (3 mg) was dissolved in 3 ml of distilled water and neutralized with 0.01N NaOH, and then the solution was lyophilized to give a test sample.

The PBS(−) and PBS(+) solutions used in protocol II were prepared as follows:

Dulbecco's phosphate buffered saline (PBS) solution was used. Preparation of PBS(−) solution: One PBS(−) tablet (Flow Laboratories, Cat. No. 28-103-05) was dissolved in 100 ml distilled water, and the solution was autoclaved for 10 minutes at 115° C. This solution contains 0.2 g/L of KCl, 0.2 g/L of KH₂PO₄, 8 g/L of NaCl, and 1.15 g/L of Na₂HPO₄. Preparation of PBS(+) solution: One PBS(−) tablet was dissolved in 80 ml distilled water; 10 mg of CaCl₂ was dissolved in 10 ml distilled water; 10 mg of MgCl₂, 6H₂O was dissolved in 10 ml distilled water. These solution were separately autoclaved, as described above, and mixed when cooled.

The water solubility of representative compound is given in Table 3.

TABLE 3

| Compound | Water Solubility | |
|---|---|---|
| | Method | Solubility (μg/ml) |
| Ex. 1 | II (−)* | >30,000 |
| | II (+) | >31,000 |
| Ex. 2 | II (−) | 11,000 |
| Ex. 3 | II (−) | 11,000 |
| Ex. 7** | II (−) | 3 |
| Pradimicin A | II (−) | 17 |
| Ex. 9 | II (+) | >32,000 |
| Ex. 10 | II (+) | 1,000 |
| Ex. 11 | II (+) | 250 |
| Pradimicin A | II (+) | 81 |
| Ex. 4 | I | >10,000 |
| Ex. 5 | I | >4,000 |
| Ex. 6 | I | >4,000 |
| Ex. 15 | I | 2,000 |
| Ex. 18 | I | 4,000 |

TABLE 3-continued

| Compound | Water Solubility | |
|---|---|---|
| | Method | Solubility (μg/ml) |
| Ex. 21 | I | 2,000 |
| Ex. 22 | I | 5,000 |
| Ex. 23 | I | 500 |
| Pradimicin A | I | 17 |
| Pradimicin B | I | 70 |

*(−): PBS (−);
(+): PBS (+).
**Very soluble in distilled water at pH 9 to give a clear solution but decomposed to generate pradimicin C at pH 7.0.

Compounds of the present invention have been shown to possess activity against various fungi. Furthermore, they are more water soluble than parent pradimicins.

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions, or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, slaves, tinctures, and the like. Unit dosage forms may be prepared using methods generally known to those skilled in the art of pharmaceutical formulations.

It will be appreciated that, when treating a host infected with a fungus susceptible to the antibiotics of this invention, the actual preferred route of administration and dosage used will be at the discretion of the attending clinician skilled in the treatment of fungal infection and will vary according to the causative organism, its sensitivity to the antibiotic, severity and site of the infection, and patient characteristics, such as age, body weight, rate of excretion, concurrent medications, and general physical condition.

The following examples illustrate the invention without limiting its scope which is defined by the claims appended to this specification.

EXAMPLE 1. Preparation of N-(carboxymethyl) pradimicin A (II, R¹=CH₃, R²=β-D-xylosyl, R³=CH₃, R⁴=-CH₂CO₂H)

Iodoacetic acid (75 mg, 0.4 mmol) was added to a mixture of pradimicin A HCl (50 mg, 0.057 mmol) and BSA (0.25 ml, 1 mmol) in methylene chloride (1 ml), and the mixture was refluxed overnight. Methanol (5 ml) and 1N HCl (1 ml) were then added thereto. The reaction mixture was concentrated under reduced pressure, and the oily residue was chromatographed on a C₁₈ silica gel column (prePAK cartridge (Waters), 20 mm×250 mm) eluting with water then 30% acetonitrile-water. Fractions containing the desired product were combined, concentrated, and freeze-dried to provide the title product (43 mg, 84%) as an amorphous powder.

IR γ$_{max}$ (KBr) cm⁻¹: 1725 (weak), 1628-1607, 1388, 1334, 1296, 1257, 1050.

UV $\lambda_{max}$ (1/100N NaOH) nm ($\epsilon$): 232 (32400), 318 (15000), 497 (14400).

MS (SIMS): m/z 899 (M+H)$^+$.

$^1$H NMR (DMSO-d$_6$) δ: 1.18 (3H, d, J=6.4 Hz, 5'-CH$_3$), 1.32 (3H, d, J=7.3 Hz, alanyl-CH$_3$), 2.28 (3H, s, 3-CH$_3$), 2.61 (3H, s, N-CH$_3$), 3.69 (1H, dd, J=5.3 & 11 Hz, 5''-H), 3.95 (3H, s, OCH$_3$), 4.39 (1H, qui, J=7.3 Hz, alanyl-CH), 4.43 (1H, d, J=8 Hz, 1''-H), 4.43 (1H, d, J=12 Hz, 5-H), 4.56 (1H, br-d, J=12 Hz, 6-H), 4.60 (1H, d, J=8 Hz, 1'-H), 4.99 (2H, br)*, 5.59 (1H, br)*, 6.02 (1H, br)*, 6.93 (1H, d, J=2 Hz, 10-H), 7.05 (1H, s, 4-H), 7.28 (1H, d, J=2 Hz, 12-H), 8.04 (1H, s, 7-H), 8.58 (1H, d, J=7 Hz, CONH)*, 12.0 (1H, br)*, 12.90 (1H, s)*, 13.80 (1H, br)*.

*Disappeared by addition of D$_2$O.

EXAMPLE 2. Preparation of N-(carboxymethyl) pradimicin A (II, R$^1$=CH$_3$, R$^2$=β-D-xylosyl, R$^3$=CH$_3$, R$^4$=-CONH$_2$)

Iodoacetamide (150 mg, 0.81 mmol) was added to a mixture of pradimicin A HCl (100 mg, 0.11 mmol) and BSA (0.56 ml, 2.2 mmol) in methylene chloride (4 ml), and the mixture was refluxed overnight. Additional BSA (0.56 ml) and iodoacetamide (150 mg) were then added to the reaction mixture and the mixture was refluxed for an additional 5 hours. The reaction mixture was treated with 1N HCl (3 ml) and methanol (10 ml) and concentrated under reduced pressure. The residue was chromatographed on a C$_{18}$ silica gel column (20 mm×200 mm) eluting with water then 30% acetonitrile-water. Fractions containing the desired product were combined, concentrated, and freeze-dried to provide the title compound (81 mg, 82%) as a deep red amorphous powder. M.P. 225° C. (dec.).

IR $\gamma_{max}$ (KBr) cm$^{-1}$: 1607, 1296, 1063.

UV $\lambda_{max}$ (1/100N NaOH) nm ($\epsilon$): 319 (15200), 497 (14600).

MS (SIMS): m/z 898 (M+H)$^+$.

$^1$H NMR (DMSO-d$_6$) δ: 1.20 (3H, d, J=6 Hz, 5'-CH$_3$), 1.32 (3H, d, J=7.3 Hz, alanyl-CH$_3$), 2.29 (3H, s, 3-CH$_3$), 2.56 (3H, s, N-CH$_3$), 3.71 (1H, dd, J=5 & 12 Hz, 5''-H), 3.95 (3H, s, OCH$_3$), 4.38 (1H, qui, J=6 Hz, alanyl-CH), 4.45 (1H, d, J=8 Hz, 1''-H), 4.46 (1H, d, J=12 Hz, 5-H), 4.54 (1H, br-d, J=12 Hz, 6-H), 4.61 (1H, d, J=8 Hz, 1'-H), 5.20 (2H, br)*, 5.63 (1H, br)*, 6.05 (1H, br)*, 6.93 (1H, d, J=2 Hz, 10-H), 7.05 (1H, s, 4-H), 7.20 (2H, br, CONH$_2$)*, 7.29 (1H, d, J=2 Hz, 12-H), 8.05 (1H, s, 7-H), 8.58 (1H, d, J=7 Hz, CONH)*, 12.55 (1H, br)*, 12.90 (1H, s)*, 13.80 (1H, br)*.

*Disappeared by addition of D$_2$O.

EXAMPLE 3. Preparation of N-(ethoxycarbonylmethyl) pradimicin A (II, R$^1$=CH$_3$, R$^2$=β-D-xylosyl, R$^3$=CH$_3$, R$^4$=-CH$_2$CO$_2$C$_2$H$_5$)

The procedure of Example 1 was repeated using pradimicin A HCl (50 mg, 0.057 mmol), BSA (0.28 ml, 1.1 mmol), and ethyl iodoacetate (0.20 ml, 1.7 mmol) to provide the title compound (39 mg, 74%) as a deep red amorphous powder. M.P. 225° C. (dec.).

IR $\gamma_{max}$ (KBr) cm$^{-1}$: 1737, 1607, 1296, 1066.

UV $\lambda_{max}$ (1/100N NaOH) nm ($\epsilon$): 320 (15600), 498 (15100).

MS (SIMS): m/z 927 (M+H)$^+$.

$^1$H NMR (DMSO-d$_6$) δ: 1.17 (3H, d, J=7 Hz, 5'-CH$_3$), 1.18 (3H, t, J=7 Hz, CH$_2$CH$_3$), 1.33 (3H, d, J=7 Hz, alanyl-CH$_3$), 2.28 (3H, s, 3-CH$_3$), 2.61 (3H, s, N-CH$_3$), 3.95 (3H, s, OCH$_3$), 4.06 (2H, m, CH$_2$CH$_3$), 4.39 (1H, qui, J=7 Hz, alanyl-CH), 4.52 (1H, br-d, J=12 Hz, 6-H), 4.59 (1H, d, J=8 Hz, 1'-H), 5.00 (3H, br)*, 5.58 (1H, br)*, 5.99 (1H, br)*, 6.91 (1H, d, J=2 Hz, 10-H), 7.04 (1H, s, 4-H), 7.28 (1H, d, J=2 Hz, 12-H), 8.03 (1H, s, 7-H), 8.59 (1H, d, J=7 Hz, CONH)*, 12.55 (1H, br)*, 12.92 (1H, s)*, 13.90 (1H, br)*.

*Disappeared by addition of D$_2$O.

EXAMPLE 4. Preparation of N-(carboxymethyl) pradimicin B (II, R$^1$=CH$_3$, R$^2$=H, R$^3$=CH$_3$, R$^4$=-CH$_2$CO$_2$H)

To a solution of pradimicin B (1.00 g, 1.41 mmol) and glyoxylic acid monohydrate (2.13 g, 23.1 mmol) in water (40 ml) was added 1N NaOH (20 ml, 20 mmol) to dissolve. This solution was diluted with acetonitrile (40 ml) and stirred at room temperature for 10 minutes. To this was added sodium cyanoborohydride (0.353 g, 5.6 mmol) and the mixture was stirred at room temperature for 1 hour. Acetonitrile was removed in vacuo, and the mixture was diluted with water (20 ml) and acidified to pH 3 by addition of 1N HCl (20 ml). The precipitate formed was centrifuged, washed with water (2 ×20 ml), suspended in a small amount of water (2 ml), and lyophilized to obtain 960 mg of crude title compound as red powder. This was dissolved in water (5 ml) containing 1N NaOH (1.8 ml) by sonication and purified by column chromatography (reverse phase silica gel, Lichroprep RP-18, 40–63, μm, EM Science) eluting with water. Appropriate fractions were combined, concentrated, and acidified to pH 3 by addition of 1N HCl. The precipitate formed was collected by centrification to obtain 139 mg of the title compound. Repeated column purification of the contaminated fractions gave a total of 669 mg (0.833 mmol, yield 59.1%) of the title compound.

Rt. 1.90 minutes (purity 93%, HPLC, column: Microsorb Short One C$_{18}$, eluent: 50% buffer (0.15% KH$_2$PO$_4$, pH 3.5)/acetonitrile-H$_2$O (4:1), flow rate: 1.2 ml/minute).

IR (KBr) $\gamma$max: 3420, 1735, 1630 cm$^{-1}$.

UV (MeOH:H$_2$O; 1:1) $\lambda$max: 234 ($\epsilon$27,000), 290 ($\epsilon$22,300), 466 nm ($\epsilon$9,640).

MS (FAB): m/z 767 (M+H)$^+$; HRMS: calcd. for C$_{37}$H$_{39}$N$_2$O$_{16}$ (M+H)$^+$767.2300, found 767.2283.

$^1$H NMR (300 MHz, DMSO-d$_6$) δ(ppm): 1.17 (3H, d, J=6.3 Hz, 5'-Me), 1.31 (3H, d, J=7.3 Hz, 17-Me), 2.27 (3H, s, 3-Me), 2.67 (3H, s, N-Me), 3.2–4.0 (6H, m, 4'-H, 2'-H, 3'-H, 5'-H, CH$_2$), 3.93 (3H, s, 11-OMe), 4.3–4.6 (4H, m, 17-H, 5-H 6-H, 1'-H), 5.54 (br s, exchanged with D$_2$O), 6.14 (s, exchanged with D$_2$O), 6.93 (1H, s, 10-H), 7.06 (1H, s, 4-H), 7.27 (1H, d, J=2.3 Hz, 12-H), 8.05 (1H, s, 7H), 8.55 (1H), d, J=7.2 Hz, CONH, exchanged with D$_2$O), 12.85 (1H, s, exchanged with D$_2$O).

$^{13}$C-NMR (300 MHz, DMSO-d6CDCl$_3$) δ(ppm): 17.1, 17.3 (5'-Me, 17-Me), 19.4 (3-Me), 42.6 (N-Me), 47.8 (C-17), 56.5 (11-OMe), 57.8 (NCH$_2$), 65.3 (C-5'), 71.4 (C-2'), 71.8 (C-6), 72.7, 73.6 (C-4', C-3'), 8.08 (C-5), 105.3 (C-1'), 106.7 (C-10), 107.7 (C-12), 110.1 (C-8a), 114.1 (C-7), 115.8 (C-4), 126.4 (C-2), 127.3 (C- ), 131.5 (C-14a), 134.6 (C-7a), 137.3 (C-4a), 138.5 (C-12a), 148.0 (C-6a), 151.6 (C- ), 157.8 (C-1), 164.8 (C-9), 166.0 (C-11), 167.2 (C- ), 173.3 (C- ), 174.2 (C- ), 185.2 (C-13), 186.9 (C-8).

EXAMPLE 5. Preparation of N-(carboxymethyl) pradimicin B (II, R$^1$=CH$_3$, R$^2$=H, R$^3$=CH$_3$, R$^4$=-CH$_2$CONH$_2$)

To a suspension of pradimicin B (100 mg, 0.14 mmol); 85% pure by HPLC) in 1,2-dichloroethane (5 ml) was injected BSA (0.6 ml, 2.4 mmol), and the mixture was stirred at 70° C. under a nitrogen atmosphere for 1.5 hours. To this dark solution was added iodoacetamide (189 mg, 0.99 mmol) and the mixture stirred at 100° C. for 6 hours. The mixture was concentrated in vacuo, and the residue dissolved in acetonitrile (10 ml), and the solution was treated with 1N HCl (1.5 ml) for 10 minutes. The precipitate formed was collected and purified by column chromatography (reverse phase silica gel, Lichroprep, RP-18 EM Science) eluting with 35% acetonitrile/$H_2O$ to obtain 51 mg (0.067 mmol, yield 48%) of the title compound as dark orange powder: Rt 3.29 minutes (purity 87.5%; HPLC, eluent: A/B=1/1 where A=50% acetonitrile/0.15% potassium phosphate buffer, pH 3.5, B=80% acetonitrile/$H_2O$, other conditions: the same as given in Example 4).

IR (KBr) γmax: 3423, 1697, 1625 cm$^{-1}$.
UV (MeOH:$H_2O$; 1:1) λmax: 234 (ε29,300), 290 (ε24,000), 470 (ε10,100).
MS (FAB): m/z 766 (M+H)$^+$.
$^1$H NMR (300 MHz, DMSO-$d_6$) δ(ppm): 1.19 (3H, d, J=7.2 Hz, 5'-Me), 1.32 (3H, d, J=6.8 MHz, 17-Me), 2.28 (3H, s, 3-Me),2.63 (3H, brs, N-Me), 3.2-3.8 (m), 3.93 (3H, s, 11-OMe), 4.3-4.6 (4H, m) 5.5 (1H, br, $D_2O$ exchangeable), 6.0 (1H, br, $D_2O$ exchangeable), 6.89 (1H, d, J=2 Hz, 10-H), 7.03 (1H, s, 4-H), 7.25 (2H, br, 12-H and one of CONH$_2$, partially $D_2O$ exchangeable), 7.6 (1H, brs, one of CONH$_2$, $D_2O$ exchangeable), 8.0 (1H, s, 7-H), 8.62 (1H, d, J=7 Hz, CONH, $D_2O$ exchangeable), 12.92 (1H, s, $D_2O$ exchangeable).

EXAMPLE 6. Preparation of N-(ethoxycarbonylmethyl) pradimicin B (II, R$^1$=CH$_3$, R$^2$=H, R$^3$=CH$_3$, R$^4$=-CH$_2$CO$_2$C$_2$H$_5$)

The procedure of Example 5 was repeated using pradimicin B (100 mg, 0.14 mmol; 85% purity by HPLC), BSA (0.6 ml, 2.4 mmol), and ethyl iodoacetate (0.12 ml, 1.01 mmol); and as eluent for column chromatography water, 20% acetonitrile/$H_2O$ and 40% acetonitrile/$H_2O$ to provide the title compound (32 mg, 29%) as orange powder: Rt 5.63 minutes (purity >95%; HPLC, eluent: 50% acetonitrile/0.15% potassium phosphate buffer, pH 3.5, other conditions: same as given in Example 4).

IR (KBr) γmax: 3426, 1731, 1635, 1608 cm$^{-1}$.
UV (MeOH:$H_2O$; 1:1) λmax: 234 (ε32,00), 290 (ε26,000), 468 nm (ε11,000).
MS (FAB): m/z 795 (M+H)$^+$; HRMS: calcd. for C$_{39}$H$_{43}$N$_2$O$_{16}$ (M+H)$^+$795.2613, found 795.2594.
$^1$H NMR (300 MHz, DMSO-$d_6$) δ(ppm): 1.22 (3H, t, J=7 Hz, CH$_3$CH$_2$-), 1.29 (3H, d, J=7.3 Hz, 5'-Me), 1.37 (3H, d, J=6.6 Hz, 17-Me), 2.28 (3H, s, 3-Me), 3.12 (3H, s, N-Me), 3.85 (1H, m), 3.92 (3H, s, 11-OMe), 3.93-3.98 (2H, m), 4.08-4.6 (5H, m), 4.7 (1H, d, =6.7 Hz, 1'-H), 6.9 (1H, d, J=2 Hz, 10-H), 7.03 (1H, s, 4-H), 7.26 (1H, d, J=2 Hz, 12-H), 8.06 (1H, s, 7-H), 8.54 (1H, d, J=7 Hz, CONH, $D_2O$ exchangeable), 12.8 (1H, s, $D_2O$ exchangeable).

EXAMPLE 7. Preparation of N-(sodiosulfomethyl) pradimicin C (II, R$^1$=CH$_3$, R$^2$=β-D-xylosyl, R$^3$=H, R$^4$=-CH$_2$SO$_2$Na)

To a solution of pradimicin C (50 mg, 0.058 mmol) in water (10 ml) were added sodium bicarbonate (14.6 mg, 0.174 mmol), and hydroxymethanesulfonic acid sodium salt (11.7 mg, 0.087 mmol). The whole mixture was stirred for 30 minutes at room temperature and lyophilized to yield 80 mg of a solid. M.P.>100° C. (grad. dec.).

IR γmax (KBr) cm$^{-1}$: 1618, 1623.
UV λmax (1/100N NaOH) nm (E$_{1cm}^{1}$%): 319 (115), 498 (112).
$^1$H NMR (400 MHz, DMSO-$d_6$) δ: 1.20 (3H, d, J=6.5 Hz, 5'-CH$_3$), 1.30 (3H, d, J=6.9 Hz, CH-CH$_3$), 2.23 (3H, s, 3-CH$_3$), 3.90 (3H, s, 11-OCH$_3$), 4.59 (1H, d, J=7.7 Hz, 1'-H), 6.71 (1H, d, J=2.0 Hz, 10-H), 6.93 (1H, s, 4-H), 7.13 (1H, d, J=2.0 Hz, 12-H), 7.71 (1H, s, 7-H).

EXAMPLE 8. Preparation of N-(sodiosulfomethyl) pradimicin A (II, R$^1$=CH$_3$, R$^2$=β-D-xylosyl, R$^3$=CH$_3$, R$^4$=-CH$_2$SO$_2$Na)

To a suspension of pradimicin A HCl (50 mg, 0.057 mmol) in $H_2O$ (5 ml) were added sodium bicarbonate (9.6 mg, 0.114 mmol), and hydroxymethanesulfonic acid sodium salt monohydrate (8.7 mg, 0.057 mmol), and the whole mixture was stirred at room temperature for 2 hours and then lyophilized to afford a sample (63 mg; theoretical=59 mg), which was found by proton NMR to be a mixture of the title compound and pradimicin A in a ratio of approximately 1:3. Complete separation of the two components was not successful. M.P. >220° C.

IR γmax (KBr) cm$^{-1}$: 3413, 1618, 1603, 1442, 1384, 1355, 1290, 1256.
UV λmax ($H_2O$) nm (E$_{1cm}^{1}$%): 222 (241), 276 (197).
$^1$H NMR (DMSO-$d_6$+$D_2O$) δ: 1.14 and 1.23 [total 3H (ca. 3:1), each d, J$_{5',Me}$=6.4 Hz, 5'-Me], 1.31 (3H, d, J$_{17,Me}$=6.8 Hz, 17-Me), 2.22 and 2.24 [total 3H (ca. 1:3), each s, 4'-NMe], 2.40 (3H, s, 3-Me), ca. 3.0-3.2 (3H, m, 2''-H, 5''-Hax, and 3''-H), ca. 3.6 (2H, m, 2'-H, and 3'-H), 3.70 (1H, dd, J$_{5''ax,5''eq}$=11.2 Hz, J$_{4'',5''eq}$=5.4 Hz, 5''-Heq), 3.90 (3H, s, 11-OMe), 4.10 (1H, q, 17-H), 4.36 (1H, d, J$_{1'',2''}$=7.3 Hz, 1''-H), 4.39 (1H, d, J$_{5,6}$=10.8 Hz, 5-H), 4.44 (1H, d, J$_{10,12}$=2.4 Hz, 10-H), 6.93 (1H, s, 4-H), 7.14 (1H, d, 12-H), 7.69 (1H, s, 7-H).

EXAMPLE 9. Preparation of N-formyl pradimicin A (II, R$^1$=CH$_3$, R$^2$=β-D-xylosyl, R$^3$=CH$_3$, R$^4$=-COH)

To a mixture of pradimicin A HCl (100 mg, 0.11 mmol) and BSA (0.50 ml, 2 mmol) in methylene chloride (2 ml) was added acetic formic anhydride (0.1 ml), and the mixture was stirred overnight at room temperature. To the mixture was added 1N HCl (1 ml) and MeOH (3 ml), and the mixture was concentrated under reduced pressure. The residue was dissolved in a small amount of aq. NaHCO$_3$ and chromatographed on a column of C$_{18}$-silica gel (20 mm×150 mm) using water and then 10% acetonitrile-water as eluent. The acetonitrile fractions were checked by HPLC, and desired fractions were combined, concentrated, and freeze-dried to provide the title compound (78 mg, 82%) as deep red amorphous powder. M.P. 250° C. (dec.).

IR γmax (KBr) cm$^{-1}$: 1643-1607, 1445, 1162.
UV λmax (1/100N NaOH) nm (ε): 319 (14300), 497 (13900).
MS (SIMS): m/z 891 (M+Na)$^+$.
$^1$H NMR (DMSO-$d_6$) δ: 1.04 (3H, d, J=6.4 Hz, 6'-H), 1.33 (3H, d, J=7.2 Hz, alanyl-CH$_3$), 2.26 (3H, s, 3-CH$_3$), 2.97 (3H, s, N-CH$_3$), 3.68 (1H, dd, J=5 & 12 Hz, 5''-H), 3.90 (3H, s, OCH$_3$), 4.34 (1H, qui, J=7.2 Hz, alanyl-CH), 4.40 (1H, d, J=8 Hz, 1''-H), 4.44 (2H, m, 5,6-H), 4.74 (1H, d, J=8 Hz, 1'-H), 6.71 (1H, d, J=2.1 Hz, 10-H), 6.85 (1H, s, 4-H), 7.11 (1H, d, J=2.1 Hz, 12-H), 7.75 (1H, s, 7-H), 7.92 (s, CHO), 8.65 (1H, br, CONH)*, 13.20 (1H, br)*, 15.15 (1H, br)*,

*Disappeared by addition of D$_2$O.
**Accompanied with a signal due to the minor rotamer.

EXAMPLE 10. Preparation of N-glycyl pradimicin A (II, R$^1$=CH$_3$, R$^2$=β-D-xylosyl, R$^3$=CH$_3$, R$^4$=-COCH$_2$NH$_2$)

To a solution of pradimicin A HCl (105 mg, 0.12 mmol) and BSA (0.6 ml, 2.4 mmol) in dry methylene chloride (3 ml) was added 1-benzotriazolyl ester of N-t-BOC-glycine (350 mg, 1.2 mmol). the mixture was heated under reflux overnight and then cooled to room temperature. A 1M solution of tetrabutylammonium fluoride in tetrahydrofuran (2.5 ml) was added, and the mixture was stirred for 30 minutes at room temperature and then concentrated at reduced pressure. The residue was diluted with H$_2$O, acidified with 1N HCl to pH 5, and the solid formed was collected by filtration. The filtrate was extracted with ethyl acetate, the solvent evaporated, and the residue combined with the solid previously obtained. The mixture was chromatographed on a C$_{18}$ column using 40% acetonitrile-pH 3.5 buffer. Fractions containing the desired product were combined and evaporated under reduced pressure. The residue was dissolved in ethyl acetate and washed with water. The organic layer was dried with Na$_2$SO$_4$ and evaporated to give 52 mg (46%) of the N-t-BOC-glycyl derivative of pradimicin A.

$^1$H NMR (400 MHz, DMSO-d$_6$) δ: 1.03 (3H, d, J=6.0 Hz, 6'-H)**, 1.33 (3H, d, J=7.3 Hz, 17-CH$_3$), 1.37 and 1.38 (9H, s, tert-Butyl), 2.29 (3H, s, 3-CH$_3$), 3.0–3.2 (5H, m, 4'-H), 2''-5''-H), 3.71 (1H, dd, J=5.4 and 11 Hz, 5''-H), 3.95 (3H, s, 11-OCH$_3$), 4.39 (1H, qui, J=7.3 Hz, 17-H), 4.4–4.6 (3H, m, 5-H, 6-H, 1''-H), 4.71 (1H, d, J=6.8 Hz, 1'-H), 4.9–4.1 (3H, br-s, OH)*, 5.6–5.8 (1H, br-s, OH)*, 5.99 (1H, br-s, OH)*, 6.91 (1H, s, 10-H), 7.02 (1H, s, 4-H), 7.27 (1H, s, 12-H), 8.00 (1H, s 7-H), 8.62 (1H, s, 16-NH)*, 12.57 (1H, br-s, OH)*, 12.94 (1H, s, OH)*.
*Disappeared by addition of D$_2$O.
**Accompanied with a signal due to the minor rotamer.

A solution of N-(N-t-BOC-glycyl-pradimicin A (52 g, 0.055 mmol) in trifluoroacetic acid (TFA) (1 ml) was stirred for 30 minutes at room temperature. After TFA had been evaporated, isopropyl ether was added to the residue and the precipitate formed was collected by filtration. The mixture was purified by preparative HPLC (Nihon seimitsu, column NS-20250, solvent 30% MeCN-pH 3.5 buffer), followed by chromatography on a C$_{18}$ silica gel column using 25–30% acetonitrile-H$_2$O as eluent to give the title compound (23.0 mg, yield 46%) after lyophilization of the eluate. M.P. >220° C. (dec.).

IR γ$_{max}$ (KBr) cm$^{-1}$: 3413, 2390, 1620, 1380, 1332, 1054.

UV λ$_{max}$ (0.01N NaOH) nm (ε): 320 (12,300), 497 (12,000).

MS (FAB): m/z 900 (M+3H)$^+$.

$^1$H NMR (400 MHz, DMSO-d$_6$) δ: 1.08 (3H, d, J=6.4 Hz, 6'-H), 1.33 (3H, d, J=7.3 Hz, 17-CH$_3$), 2.26 (3H, s), 3.69 (1H, dd, J=5.6 & 11.1 Hz, 5''-H), 3.91 (3s, d, 11-OCH$_3$), 4.25 (1H, br-m, 17-H), 4.4–4.5 (2H, 5-H, 6-H), 4.48 (1H, d, J=7.7 Hz, 1''-H), 4.73 (1H, d, J=7.3 Hz, 1'-H)**, 5.0–5.15 (3H, brs, OH)*, 5.72 (1H, br-s, OH)*, 5.80 (1H, br-s, OH)*, 6.71 (1H, d, 2.6 Hz, 10-H), 6.83 (1H, s, 4-H), 7.13 (1H, d, J=2.6 Hz, 12-H), 7.74 (1H, s, 7-H), 8.6 (1H, br, 16-NH)*,
*Disappeared by addition of D$_2$O.
**Accompanied with a signal due to the minor rotamer.

EXAMPLE 11. Preparation of N-(β-alanyl) pradimicin A (II, R$^1$=CH$_3$, R$^2$=β-D-xylosyl, R$^3$=CH$_3$, R$^4$=-CO(CH$_2$)$_2$NH$_2$)

To a solution of pradimicin A HCl (100 mg, 0.11 mmol) and BSA (0.6 ml, 2.4 mmol) in dry methylene chloride (5 ml) was added 1-benzotriazolyl ester of N-t-BOC-β-alanine (349, mg, 1.1 mmol). the mixture was refluxed for 2 days and then cooled to room temperature. A 1M solution of tetrabutylammonium fluoride in tetrahydrofuran (3 ml) was added, and the purple colored mixture was stirred for 30 minutes at room temperature. After the solvent was evaporated under reduced pressure, ethylacetate and 10% citric acid were added to the residue. The mixture was shaken and then filtered to collect the insoluble solid, and the organic layer was separated and washed with water and brine. The insoluble solid was added to the organic layer, and the mixture was concentrated. The residue was chromatographed on a C$_{18}$ silica gel column eluting with 35–40% acetonitrile-H$_2$). The fractions containing the desired compound were combined, evaporated and extracted with ethyl acetate. The extracts were concentrated and freeze-dried from 1,4-dioxane to give 100 mg (87%) of N-t-BOC-β-alanyl derivative.

$^1$H NMR (400 MHz, DMSO-d$_6$) δ: 1.3–1.4 (tert-butyl), 2.28 (3H, s, 3-CH$_3$), 3.71 (1H, dd, J=5.4 and 11 Hz, 5''-H), 3.93 (3H, s, 11-OMe), 4.38 (1H, qui, J=7.3 Hz, 17-H), 4.4–4.7 (3H, m, 5-H, 6-H, 1''-H), 4.70 (1H, d, J=7.3 Hz, 1'-H), 4.9–5.1 (3H, OH)*, 5.7–5.9 (2H, OH)*, 6.83 (1H, d, J=2.2 Hz, 10-H), 6.95 (1H, s, 4-H), 7.20 (1H, d, J=2.2 Hz, 12-H), 7.90 (1H, s 7-H), 8.69 (1H, br, 16-NH)*, 13.03 (1H, s, OH)*.
*Disappeared by addition of D$_2$O.
**Accompanied with a signal due to the minor rotamer.

A solution of N-(N-t-BOC-β-alanyl)pradimicin A (90 mg, 0.089 mmol) in TFA was stirred for 15 minutes at room temperature. After TFA was evaporated, the residue was chromatographed on a C$_{18}$ silica gel column eluting with 20–40% acetonitrile-H$_2$O. The fractions containing the desired compound were combined and concentrated. The residue was dissolved in a small amount of water and lyophilized to give 20 mg) (25%) of N-(β-alanyl)pradimicin A as an amorphous powder. M.P. >230° C. (dec.).

IR γ$_{max}$ (KBr) cm$^{-1}$: 3390, 1620, 1445, 1386, 1260.

UV λ$_{max}$ (0.01N NaOH) nm (ε): 318 (13,000), 498 (12,700).

MS (FAB): m/z 912 (M+H)$^+$.

$^1$H NMR (400 MHz, DMSO-d$_6$) δ: 0.95 (3H, br, 5'-CH$_3$), 1.33 (3H, d, J=7.3 Hz, 17-CH$_3$), 2.23 (3H, s, 3-CH$_3$), 3.74 (1H, dd, J=4.7 and 11 Hz, 5''-H), 3.91 (3H, s, 11-OMe), 4.2 (1H, br, 17-CH*, 4.3–4.5 (3H, m, 5-H, 6-H, 1''-H), 4.61 (1H, d, J=7.8 Hz, 1''-H)**, 4.9–5.2 (2-3H, OH)*, 5.6–5.9 (2H, OH)*, 6.71 (1H, d, J=2.1 Hz, 10-H), 6.82 (1H, s, 4-H)**, 7.13 (1H, br, 12-H), 7.73 (1H, s, 7-H), 8.22 (1H, br, 16-NH)*, 8.30 (1H, s, OH)*.
*Disappeared by the addition of D$_2$O.
**Accompanied with a signal due to the minor rotamer.

EXAMPLE 12. Preparation of N-(trans-3-methoxycarbonyl-2-propenyl) pradimicin A (II, R$^1$=CH$_3$, R$^2$=β-D-xylosyl, R$^3$=CH$_3$, R$^4$=-CH$_2$CH=CHCO$_2$CH$_3$)

To a solution of pradimicin A HCl (78 mg, 0.089 mmol) and BSA (0.44 ml, 1.8 mmol) in dry dichloromethane (3 ml) was added methyl 4-bromocrotonate (80 mg, 0.445 mmol), and the mixture was refluxed for 4 days. The solvent was evaporated, and the residue was dissolved in a mixture of methanol (3 ml) and 1N HCl (3 ml). The methanol was evaporated, and the aqueous concentrate was chromatographed on a $C_{18}$ silica gel column. The column was washed with water and then eluted with 70% aqueous acetonitrile. The desired fractions monitored by HPLC were combined, concentrated, and lyophilized to yield 55 mg (yield 66%) of the title compound. M.P.>180° C.

IR $\gamma_{max}$ (KBr) cm$^{-1}$: 1720, 1610, 1440.

UV $\lambda_{max}$ (1/100N NaOH) nm ($E_{1cm}^{1\%}$): 300 (220), 500 (223).

MS (FAB): m/z 939 (M+H)+.

$^1$H NMR (400 MHz, DMSO-d$_6$) δ(ppm): 1.13 (3H, d, J=6 Hz, 5'-Me), 1.32 (3H, d, J=7.3 Hz, 17-Me), 2.27 (3H, s, 3-Me), 3.95 (3H, s, OCH$_3$), 4.39 (1H, qui, J=7.3 Hz, alanyl-CH), 6.00 (1H, d, J=15.8 Hz, =CH-COOMe) 6.83 (1H, dt, J=15.8 and 5.5 Hz, CH$_2$-CH=CH-COOMe), 6.90 (1H, br-s, 10-H), 7.02 (1H, s, 4-H), 7.27 (1H, d, J=2.2 Hz, 12-H), 8.00 (1H, s, 7-H).

EXAMPLE 13. Preparation of
N-(trans-3-carboxy-2-propenyl) pradimicin A (II,
$R^1$=CH$_3$, $R^2$=β-D-xylosyl, $R^3$=CH$_3$,
$R^4$=-CH$_2$CH=CHCO$_2$H)

A solution of N-(trans-3-methoxycarbonyl-2-propenyl) pradimicin A in the mixture of methanol and 1N NaOH was stirred at room temperature overnight. The methanol was evaporated and the aqueous residue acidified with 1N HCl and them chromatographed to a $C_{18}$ silica gel column. The column was washed with water and eluted with 40% aqueous acetonitrile. The desired fractions monitored by HPLC were combined, concentrated, and lyophilized to yield 34 mg (yield 85%) of the title compound. M.P.>180° C.

IR $\gamma_{max}$ (KBr) cm$^{-1}$: 1610, 1450, 1390.

UV $\lambda_{max}$ (1/100N NaOH) nm ($E_{1cm}^{1\%}$): 320 (235), 500 (235).

MS (FAB): m/z 927 (M+3H)+, 949 (M+Na+2H)+.

$^1$H NMR (400 MHz, DMSO-d$_6$) δ(ppm): 1.13 (3H, d, J=6.4 Hz, 5'-Me), 1.33 (3H, d, J=7.2 Hz, 17-Me), 2.25 (3H, s, 3-Me), 2.56 (3H, s, N-Me), 3.91 (3H, s, OMe), 4.3-4.5 (3H, m, 5,6-H and 17-H), 4.60 (1H, d, J=7.7 Hz, 1'-H), 5.90 (1H, d, J=15.8 Hz, =CH-COOH), 6.72 (1H, d, J=2.1 Hz, 10-H), 6.73 (1H, dt, J=15.8 and 5.5 Hz, CH=CH-COOH), 6.86 (1H, s, 4-H), 7.12 (1H, d, J=2.1 Hz, 12-H), 7.76 (1H, s, 7-H).

EXAMPLE 14. Preparation of N-(glycyl) pradimicin B
formate salt (II, $R^1$=CH$_3$, $R^2$=H, $R^3$=CH$_3$,
$R^4$=-COCH$_2$NH$_2$)

To a stirred solution of pradimicin B methyl ester HCl (114 mg, 0.15 mmol; 80% pure by HPLC) and triethylamine (20 μL, 0.15 mmol; dried over molecular sieves 4A) in dry dimethylformamide (2 mL; dried over molecular sieves 3A) was added at room temperature N-(t-BOC) glycine N-hydroxysuccinimide ester (204 mg, 0.75 mmol; Sigma). The mixture was stirred at 22° C. under a dry nitrogen atmosphere for 12 hours and then concentrated in vacuo to near dryness. The oily residue was triturated with n-pentane several times and chromatographed (SiO$_2$; MeOH-CH$_2$Cl$_2$/5:95 to 15:85) to obtain 120 mg of crude multi-acylated material: Rt 1.84 minutes (purity 75%; HPLC, column: Microsorb Short One $C_{18}$, 4.6 nm I.D.×100 mm, 3 μm, Rainin Instrument Company, eluent: A/B=1:1, A, acetonitrile-0.15% KH$_2$PO$_4$ pH 3.5=1:1, v/v; B, acetonitrile-H$_2$O=4:1, flow rate 1.2 ml/minute, detection: UV absorption at 254 nm).

This crude multi-acylated material (80 mg) in MeOH (6.5 ml) was mixed with 0.25N NaOH (3.2 ml), and the mixture was stirred at room temperature for 6 hours. This was acidified slowly and carefully with 0.1N HCl until pH 2 (pH paper) was obtained. The cloudy mixture was diluted with H$_2$O (6.5 ml) and the MeOH removed in vacuo. The resulting precipitate was filtered, washed with H$_2$O, and dried to obtain 25 mg (0.029 mmol, yield 29%) of the title compound as crude solid: Rt 2.12 minutes (purity 75%, HPLC, conditions: the same as above).

This crude material with 75% purity (200 mg) was purified by column chromatography using the Michel-Miller High Performance Low Pressure Liquid Chromatography System (Ace Glass Inc.) on C-18 reverse phase silica gel (Whatman Partisil Prep 40 ODS-3, C-18; 1.5 cm×30 cm). The column was eluted with H$_2$O and then with 80% acetonitrile-H$_2$O to obtain 20 mg of N-(t-BOC-glycyl) pradimicin B as red powder: Rt 3.48 minutes (purity 97%; HPLC, column: Waters Radial Pak $C_{18}$, eluent: 50% (pH 4, 0.05M ammonium phosphate buffer)/(80% acetonitrile in H$_2$O), flow rate: 4 ml/minute. M.P.>170°-270° C. (slow dec.).

IR (KBr) γmax: 3420, 1730, 1630, 1610 cm$^{-1}$.

UV (MeOH: H$_2$O=1:1) λmax: 232 (ε32,200), 290 (ε26,100), 468 nm (ε11,000).

MS (FAB): m/z 866 (M+H)+, 766 (M-tBoc+2H)+, 433.

$^1$H NMR (300 MHz, DMSO-d$_6$) δ(ppm): 0.97, 1.07 (3H, 2d, J=6 Hz, 5'-Me), 1.31 (3H, d, J=7 Hz, 17-Me), 1.36 (9H, s, tBu), 2.29 (3H, s, 3-Me), 3.02, 3.14 (3H, 2s, N-Me), 3.5-4.0 (6m, 2'-H, 3'-H, 4'-H, 5'-H, CH$_2$), 3.95 (3H, s, 11-OMe), 4.38 (1H, qi, J=7 Hz, 17-H), 4.4-4.6 (2H, m, 5-H, 6-H), 4.71 (1H, br, 1'-H), 5.13, 5.42, 6.61, (3H, br, exchanged with D$_2$O), 6.16 (1H, br s, OH, exchanged with D$_2$O), 6.58 (1H, t, J=5 Hz, NH, exchanged with D$_2$O), 6.94 (1H, d, J=2 Hz, 10-H), 7.08 (1H, s, 4-H), 7.29 (1H, d, J=2 Hz, 12-H), 8.07 (1H, s, 7-H), 8.55 (1H, d, J=7 Hz, CONH, exchanged with D$_2$O), 12.84 (1H, s, exchanged with D$_2$O).

A mixture of N-(t-Boc-glycyl) pradimicin B (30 mg, 0.035 mmol, purity ~86%) in 80% formic acid (3 ml) was stirred at room temperature for 6 hours. The insoluble material was removed by filtration and the filtrate concentrated in vacuo to dryness. The residue was triturated with EtOAc and dried to obtain 20 mg (0.025 mmol, yield 70%) of the title compound as red powder: Rt 2.31 minutes (purity 80%; HPLC, 50% A/B (ammonium phosphate buffer system), flow rate 2 ml/minute; this material was free from pradimicin B, <2%).

IR (KBr) γmax: 3420, 1730, 1630, 1610 cm$^{-1}$.

UV (MeOH: H$_2$O=1:1) λmax: 234 (ε17,400), 290 (ε14,100), 464 nm (ε6,100).

MS (FAB): m/z 766 (M+H-HCO$_2$H)+.

$^1$H NMR (300 MHz, DMSO-d$_6$/D$_2$O DCl) δ(ppm): 1.00, 1.08 (3H, 2d, J=6 Hz, 5'-Me), 1.32 (3H, d, J=7 Hz, 17-Me), 2.23 (3H, s, 3-Me), 3.13 (3H, br, N-Me), 3.71 (3H, s, 11-OMe), 3.7-4.0 (4H, m, 2'-H, 3'-H, 4'-H, 5'-H), 4.1-4.8 (6H, m, 17-H, 5-H, 6-H, 1'-H, CH$_2$), 6.60 (1H, br, s, 10-H), 7.00 (1H, s, 4-H), 7.09 (1H, br s, 12-H), 7.83 (1H, s, 7-H), 8.08 (1H, s, HCO$_2$).

EXAMPLE 15. Preparation of N-(N,N-dimethylglycyl) pradimicin B (II, $R^1=CH_3$, $R^2=H$, $R^3=CH_3$, $R^4=$-COCH$_2$N(CH$_3$)$_2$ To a stirred solution of pradimicin B methyl ester HCl (500 mg, 0.66 mmol; 81% pure by HPLC) and triethylamine (92.4 µL, 0.66 mmol) in dry dimethylformamide (12 ml, dried over molecular sieves 3A) was added at room temperature N,N-dimethylglycine N-hydroxysuccinimide ester (1.68 g, 8.4 mmol), and the mixture was stirred at ca. 40° C. for 24 hours. To this mixture, an additional amount of N,N-dimethylglycine N-hydroxysuccinimide ester (1.68 g, 8.4 mmol) was added, and the mixture stirring compound contained at ca. 45° C. for an additional 48 hours. The solvent was removed in vacuo, and the residue was triturated repeatedly with pentane then ether. This material was dissolved in a mixture of MeOH (30 ml) and H$_2$O (20 ml), and to this was added a cold solution of NaOH (1.06 g) in H$_2$O (15 ml over a period of 15 minutes. The mixture was stirred at room temperature for 2 hours, neutralized to pH 7 by addition of H$_3$PO$_4$ in an ice-bath, and the precipitate was removed. The filtrate was concentrated, and the residue was purified by column chromatography (reverse phase silica gel, Whatman Partisil Prep 40 ODS-3, C-18). The column was eluted with H$_2$O first and then with 50% acetonitrile/H$_2$O to obtain 86 mg (0.10 mmol, yield 15%) of the title compound as reddish brown powder: Rt 5.36 minutes (purity 74%; HPLC, column: Waters Radial PAK C$_{18}$, eluent: (pH 4 buffer, 0.05M ammonium phosphate)/80% acetonitrile H$_2$O)=3:2, flow rate: 2 ml/minute).

IR (KBr) $\gamma$max: 3400, 1640, 1610 cm$^{-1}$.

UV (MeOH: H$_2$O=1:1) $\lambda$max: 234 ($\epsilon$26,200), 288 ($\epsilon$21,300), 476 nm ($\epsilon$9,000).

MS (FAB): m/z 794 (M+H)$^+$; HRMS, calcd. for C$_{39}$H$_{44}$N$_3$O$_{15}$(M+H)$^+$799.2772, found 799.2774.

$^1$H NMR (300 MHz, DMSO-d$_6$) $\delta$(ppm): 0.99 (3/4H, d, J=6 Hz, 5'-Me), 1.01 (3/2H, d, J=6 Hz, 5'-Me), 1.10 (3/4H, d, J=6 Hz, 5'-Me), 1.32 (3H, d, J=7.3 Hz, 17-Me), 2.27 (3H, s, 3-Me), 2.73 (3H, s, NMe$_2$), 2.77 (3H, s, NMe$_2$), 3.10, 3.14 (3H, 2s, 4'-NMe), 3.5–4.3 (m), 3.90 (3H, s, 11-OMe), 4.3–4.5 (m, 17-H, 5-H, 6-H), 4.6–4.75 (m, 1'-H), 6.72 (1H, s, 10-H), 6.85 (1H, s, 4-H), 7.12 (1H, s, 12-H), 7.77 (1H, s, 7-H), 8.82, 8.84 (1H, 2d, J=7.2 Hz, CONH, exchanged with D$_2$O), 13.14 (1H, s, exchanged with D$_2$O).

N,N-Dimethylglycine N-hydroxysuccinimide ester was prepared by the following procedure.

To a stirred solution of N-hydroxysuccinimide (11.5 g, 0.1 mmol) and N,N-dimethylglycine (10.3 g, 0.01 mmol) in CH$_2$Cl$_2$ (200 ml) was added N,N-dicyclohexylcarbodiimide (22.1 g, 0.11 mmol), and the mixture was stirred at room temperature for 18 hours, heated at reflux for 10 minutes, and then allowed to stir for an additional 4 hours. The precipitate was removed, and the filtrate was evaporated. The oily residue was triturated with n-hexane, and the solid was extracted with anhydrous ether, removing the insolubles. Evaporation of the ether in vacuo gave 13.0 g (0.065 mmol, yield 65%) of the title compound as a white hygroscopic solid.

IR (KBr) $\gamma$max: 1780, 1710, 1650 (br) cm$^{-1}$.

MS (DCI): m/z 201 (M+H)$^+$.

$^1$H NMR (200 MHz, CDCl$_3$) $\delta$ppm: 2.40 (6H, s, NMe$_2$), 2.81 (4H, s, CH$_2$CH$_2$), 3.51 (2H, s, NCH$_2$).

EXAMPLE 16. Preparation of N-(N,N-Dimethylglycyl) pradimicin A (II, $R^1=CH_3$, $R^2=\beta$-D-xylosyl, $R^3=CH_3$, $R^4=$-COCH$_2$N(CH$_3$)$_2$ To a mixture of pradimicin A HCl (61 mg, 0.07 mmol) and BSA (0.35 ml, 1.4 mmol) in dichloromethane (1.2 ml) was added N,N-dimethylglycyl chloride HCl (55 mg, 0.35 mmol). The mixture was stirred at room temperature for 1 hour and concentrated in vacuo. The residue was dissolved in a mixture of methanol (2 ml) and 1N-HCl (1 ml). The methanol was evaporated, and the aqueous residue was chromatographed on a C$_{18}$ silica gel column. The column was washed with water and eluted with 30% aqueous acetonitrile to afford 42 mg (yield 65%) of the title compound. M.P.>190° C. (grad. dec.).

IR $\gamma_{max}$ (KBr) cm$^{-1}$: 1620 (broad).

UV $\lambda_{max}$ (1/100N NaOH) nm ($\epsilon$): 318 (15200), 497 (14600).

MS (FAB): m/z 926 (M+H)$^+$.

$^1$H NMR (400 MHz, DMSO-d$_6$) $\delta$(ppm): 1.00, 1.11 (total 3H, 2d, J=6.4 Hz, 5'-Me), 1.34 (3H, d, J=7.3 Hz, 17-Me), 2.28, 2.29 (total 3H, 2s, 3-Me), 2.67 (3H, s, N-Me), 2.72 (3H, s, N-Me), 3.90 (3H, s, N-OMe), 6.72 (1H, d, J=2.6 Hz, 10-H), 6.83 (1H, s, 4-H), 7.12 (1H, m, 12-H), 7.76 (1H, s, 7-H).

EXAMPLE 17. Preparation of N-carbamyl pradimicin B (II, $R^1=CH_3$, $R^2=H$, $R^3=CH_3$, $R^4=$-CONH$_2$)

To a stirred solution of pradimicin B methyl ester HCl (100 mg, 0.13 mmol) in acetonitrile (5 ml) was added BSA (0.6 ml, 2.4 mmol) and the mixture heated at 50° C. for 30 minutes. TO this mixture, after cooling to room temperature, was added triethylamine (18 µl, 0.13 mmol) followed by trichloromethylcarbonyl isocyanate (32 µl, 0.26 mmol). This mixture was stirred at room temperature under a dry nitrogen atmosphere for 20 hours by which time HPLC indicated the formation of a new product at Rt 4.52 minutes (HPLC, column: Waters Radical PAK C$_{18}$). The mixture was diluted with MeOH (2 ml) and treated with 1N HCl (1 ml), eluent: A/B=35/65 where A=pH 4, 0.5M ammonium phosphate buffer, B=80% acetonitrile in H$_2$O, flow rate: 3 ml/minute. The mixture was quickly concentrated in vacuo to dryness. The residue was dissolved in 5% acetonitrile in H$_2$O (10 ml) and stirred at room temperature for 18 hours. The solid formed was collected to obtain 77 mg of a mixture of N-(carbamyl)- and N-(trichloromethylcarbonylcarbamyl)desxylosyl pradimicin A methyl ester: Rt 2.06 minutes (49%) and 5.42 minutes (38%) (HPLC, conditions: the same as above).

This mixture (77 mg) was dissolved in a solution of acetonitrile (2 ml) and H$_2$O (2 ml). To this was added a solution of NaOH (10 mg) in H$_2$O (0.5 ml), and the mixture was stirred at room temperature for 30 minutes by which time HPLC indicated the reaction was complete. This was carefully acidified to pH 2.5 with dilute H$_3$PO$_4$. The precipitate was collected and purified by column chromatography (reverse phase silica gel, Partisil Prep 40 ODS-3, C-18) eluting with 80% acetonitrile/H$_2$O): (pH 4, 0.025M ammonium phosphate buffer)=1:4. The appropriate fractions were collected, acidified to pH 2.5 with dilute H$_3$PO$_4$, and concentrated to remove the acetonitrile. The precipitate formed was collected, washed with H$_2$O, and dried in vacuo to obtain 31 mg (0.041 mmol, yield 32%) of the title compound as dark red powder. M.P.>120°-270° C. (dec.).

Rt 3.99 minutes (purity 75%; HPLC, column: the same as above, eluent: A/B=55/45 where A and B were defined as above, flow rate: 2 ml/minute).

IR (KBr) γmax: 3400, 1730, (w), 1620, (br) cm$^{-1}$.

UV (MeOH: H$_2$O=1:1) λmax: 234 (ε27,700), 292 (ε22,900), 462 nm (ε9,880).

MS (FAB): m/z 752 (M+H)$^+$; HRMS, calc. for C$_{36}$H$_{38}$N$_3$O$_{15}$(M+H)$^+$752.2303, found 752.2288.

$^1$H NMR (300 MHz, DMSO-d$_6$) δ(ppm): 1.01 (3H, d, J=6 Hz, 5'-Me), 1.31 (3H, d, J=7 Hz, 17-H), 2.28 (3H, s, 3-Me), 3.01 (3H, s, N-Me), 3.66 (1H, brs), 3.77 (1H, m), 3.94 (3H, s, 11-OMe), 4.35-4.6 (5H, m, 17-H, 5-H, 6-H, 1'-H), 6.93 (1H, s, 10-H), 7.09 (1H, s, 4-H), 7.29 (1H, s, 12-H), 8.06 (1H, s, 7-H), 8.55 (1H, d, J=6.5 Hz, CONH, exchanged with D$_2$O), 12.85 (1H, s, exchanged with D$_2$O).

EXAMPLE 18. Preparation of N-(N-methylcarbamoyl) pradimicin B (II, R$^1$=CH$_3$, R$^2$=H, R$^3$=CH$_3$, R$^4$=-CONHCH$_3$)

To a stirred suspension of pradimicin B methyl ester HCl (100 mg, 0.13 mmol) in acetonitrile (5 ml) was added BSA (0.6 ml, 2.4 mmol), and the mixture heated at 50° C. for 30 minutes. To this mixture, after cooling to room temperature, was injected triethylamine (18 μl, 0.13 mmol) followed by methyl isocyanate (7.7 μl, 0.13 mmol). The mixture was stirred at room temperature under a dry nitrogen atmosphere for 2 hours, then an additional amount of methyl isocyanate (15.4 [L, 0.26 mmol) was injected, and stirring continued for another 4 hours. The mixture, diluted with MeOH (2 ml) was treated with 1N HCl (1 ml) and concentrated in vacuo to remove organic solvents. The resulting precipitate was collected, washed with water, and purified by column chromatography (reverse phase silica gel, Whatman Partisil Prep 40 ODS-3, C-18) eluting with 20% acetonitrile/pH 4, 0.025M ammonium phosphate buffer and then with 100% acetonitrile. The appropriate fractions were (acetonitrile) were concentrated in vacuo to obtain 32 mg (0.041 mmol, yield 32%) of the title compound as the methyl ester: Rt 6.00 minutes (purity 91%; HPLC, column: Waters Radial PAK C$_{18}$, eluent: A/B=1/1 where A=pH 4, 0.05M ammonium phosphate buffer, B=80% acetonitrile/H$_2$O, flow rate: 3 ml/minute).

This ester (27 mg, 0.035 mmol) was dissolved in a mixture of MeOH (1 ml) and H$_2$O (1 ml), and this was treated with a solution of NaOH (12 mg) in H$_2$O (0.3 ml) at room temperature for 1 hour by which time HPLC indicated the completion of the reaction. The mixture was acidified to pH 3 by addition of 10% H$_3$PO$_4$ and concentrated in vacuo to near dryness. The precipitate was collected, washed with H$_2$O (0.3 ml×2), and dried to obtain 24 mg (0.031 mmol, yield 89%; overall yield 28%) of the title compound as red powder. M.P.>138° C. (dec.).

Rt 2.29 minutes (purity 93%; HPLC, conditions: the same as above).

IR (KBr) γmax: 3400, 1730, (w), 1620, (br) cm$^{-1}$.

UV (MeOH: H$_2$O=1:1) λmax: 234 (ε32,200), 290 (ε26,100), 468 nm (ε11,300).

MS (FAB): m/z 766 (M+H)$^+$; HRMS, calc. for C$_{37}$H$_{40}$N$_3$O$_{15}$ (M+H)$^+$766.2459, found 766.2441.

$^1$H NMR (300 MHz, DMSO-d$_6$) δ(ppm): 1.02 (3H, d, J=6 Hz, 5'-Me), 1.34 (3H, d, J=7.3 Hz, 17-Me), 2.31 (3H, s, 3-Me), 2.59 (3H, d, J=4 Hz, NHMe), 3.03 (3H, s, NMe), 3.69 (2H, br s), 3.82 (1H, m), 3.97 (3H, s, 11-OMe), 4.35-4.6 (5H, m, 17-H, 5-H, 6-H, 1'-H), 5.00 (br), 6.17 (d, exchanged with D$_2$O), 6.96 (1H, d, J=2.4 Hz, 10-H), 7.11 (1H, s, 4-H), 7.31 (1H, d, J=2.4 Hz, 12-H), 8.08 (1H, s, 7-H), 8.57 (1H, d, J=7 Hz, CONH, exchanged with D$_2$O), 12.87 (1H, s, exchanged with D$_2$O).

EXAMPLE 19. Preparation of N-(p-toluenesulfonylcarbamyl) pradimicin B (II, R$^1$=CH$_3$, R$^2$=H, R$^3$=CH$_3$, R$^4$=-CONHSO$_2$-p-tolyl)

To a stirred suspension of pradimicin B methyl ester HCl (100 mg, 0.13 mmol) in acetonitrile (5 ml) was added BSA (0.6 ml, 2.4 mmol), and the mixture heated at 50° C. for 30 minutes. After cooling to room temperature, to this reaction mixture was added triethylamine (18 μl, 0.13 mmol) and then p-toluenesulfonylisocyanate (25.3 mg, 0.13 mmol). The mixture was stirred at room temperature under a dry nitrogen atmosphere for 5 hours. An additional p-toluenesulfonylisocyanate (ca. 10 mg) was added, and stirring continued for another 18 hours by which time HPLC indicates that ca. 80% of the product was formed. The mixture was diluted with MeOH (2 ml) and to this 1N HCl (1 ml) was added. The solution was concentrated quickly in vacuo to dryness. The suspension of the residue in H$_2$O (3 ml) was stirred for 3 hours, and the solid was collected, triturated with Et$_2$O, and dried to obtain 77 mg (0.084 mmol, yield 64%) of the methyl ester of the title compound as red solid: Rt 3.39 minutes (purity 85%; HPLC, column: Waters Radial PAK C$_{18}$, eluent: A/B=35/65 where A=pH 4, 0.05M ammonium phosphate buffer, B=80% acetonitrile in H$_2$O, flow rate 4 ml/minute).

The methyl ester (50 mg, 0.056 mmol) was suspended in a mixture of MeOH (3 ml) and H$_2$O (3 ml). To this was added a solution of NaOH (22 mg, 0.056 mmol) in H$_2$O (1 ml), and the mixture was stirred at room temperature for 1 hour. This was acidified in an ice-bath with diluted H$_3$PO$_4$ to pH 3 and then concentrated in vacuo to the volume of ca. 3 ml. The precipitate was collected, washed with H$_2$O, and dried in vacuo to obtain 34 mg (0.038 mmol, yield 67%; overall yield 43%) of the title compound as reddish powder. M.P.>125° C. (dec.).

Rt 1.61 minutes (purity 83%; HPLC, eluent: A/B=35/65 where A=pH 4, 0.05M ammonium phosphate buffer, B=80% acetonitrile in H$_2$O, other conditions: the same as above).

IR (KBr) γmax: 3400, 1720, (w), 1620, (br) cm$^{-1}$.

UV (MeOH: H$_2$O=1:1) λmax: 230 (ε35,500), 290 (ε21,300), 468 nm (ε9,000).

MS (FAB): m/z 906 (M+H)$^+$.

$^1$H NMR (300 MHz, DMSO-d$_6$) δ(ppm): 0.91, 1.05 (3H, 2br, 5'-Me), 1.32 (3H, d, J=7 Hz, 17-Me), 2.30 (3H, s, 3-Me), 2.38 (3H, s, p-Me), 2.89, 3.12 (3H, 2s, NMe), 3.94 (3H, s, 11-OMe), 4.42-4.7 (m, 17-H, 5-H, 6-H, 1'-H), 6.91 (1H, s, 10-H), 7.03 (1H, s, 4-H), 7.26 (1H, s, 12-H), 7.36 (2H, d, J=8 Hz, ArHs), 7.77 (2H, d, J=8 Hz, ArHs), 8.02 (1H, s, 7-H), 8.59 (1H, d, J=6.5 Hz, CONH, exchanged with D$_2$O), 12.89 (1H, s, exchanged with D$_2$O).

EXAMPLE 20. Preparation of N-(L-glutamyl) pradimicin B formate salt (II, R$^1$=CH$_3$, R$^2$=H, R$^3$=CH$_3$, R$^4$=-COCH(NH$_2$)(CH$_2$)$_2$CO$_2$H)

To a stirred suspension of pradimicin B methyl ester HCl (760 mg, 1.0 mmol; 80% pure by HPLC) in DMF (5 ml, dried over molecular sieves 3A) was added triethylamine (0.14 ml, 1.0 mmol), followed by N-t-Boc-(L)- glutamic acid δ-benzyl α-N-hydroxy-succinimide ester (2.60 g, 6.0 mol; prepared from N-t-Boc-(L)-glutamic acid δ-benzyl ester. The resulting dark red mixture was stirred at 35° C. for 24 hours and concentrated in vacuo to near dryness. The residue was triturated several times with n-pentane, and chromatographed on silica gel (MeOH-CH$_2$Cl$_2$/5:95 to 20:80) to give 1.0 of semi-pure multi-acylated material. This semi-pure material (1.0 g) in MeOH (10 ml) and H$_2$O (5 ml) was mixed with a solution of NaOH (280 mg) in H$_2$O (5 ml). The mixture was stirred at rom temperature for 6 hours. This was acidified to pH~3 with 5% H$_3$PO$_4$, and the precipitate formed was filtered and dried to obtain 258 mg of crude solid. This was purified by column chromatography as described before C$_{18}$ column, A:B=70:30 to 50:50; A, B defined as before). Appropriate fractions were combined, acidified to pH ca. 3, and the precipitate was filtered and dried to obtain 27 mg (0.029 mmol, yield 2.9%) of the title compound as red powder: Rt 7.00 minutes (purity 95%; HPLC, 50% A/B, flow rate: 2 ml/minute).

IR (KBr) γmax: 3420, 1730, 1630, 1610 cm$^{-1}$.

UV (MeOH: H$_2$O=1:1) λmax: 234 (ε35,700), 296 (ε29,000), 464 nm (ε12,200).

MS (FAB): m/z 938 (M+H)$^+$, 838 (M-t-Boc+2H), 443.

$^1$H NMR (300 MHz, DMSO-d$_6$) δ(ppm): 0.95, 1.12 (3H, 2d, J=6 Hz, 5'-Me), 1.33 (3H, d, 17-Me), 1.34, 1.37 (9H, 2s, tBu), 1.65, 1.83, 2.20 (2H, m, CH$_2$), 2.30 (3H, s, 3-Me), 3.02 (s, NMe), 3.3, 3.73, 3.85 (6H, m, 2'-H, 3'-H, 4'-H, 5'-H, CH$_2$CO), 3.94 (3H, s, 11-OMe), 4.2-4.75 (5H, m, 17-H, CHCO, 5-H, 6-H, 1'-H), 5.27, 5.65, 6.16 (3H, br, exchanged with D$_2$O), 6.94 (1H, d, J=2.5 Hz, 10-H), 7.09 (1H, s, 4-H), 7.29 (1H, d, J=2.5 Hz, 12-H), 8.07 (1H, s, 7-H), 8.56 (1H, d, J=7 Hz, 16-NH, exchanged with D$_2$O), 12.31 (br, exchanged with D$_2$O), 12.85 (1H, s, exchanged with D$_2$O), 13.78 (br, exchanged with D$_2$O).

A mixture of N-t-Boc-Glu-pradimicin B (29 mg, 0.031 mmol; 95% pure by HPLC) in 75% (v/v) HCO$_2$H/H$_2$O (4 ml) was stirred at ca. 30° C. for 5 hours. This was concentrated in vacuo to dryness, and the residue was triturated with EtOAc to obtain 22 mg (0.025 mmol, yield 80%) of the title compound as dark red solid: Rt 6.8 minutes (HPLC, eluent A/B=40:60, flow rate: 0.5 ml/minute).

IR (KBr) γmax: 3420, 1740, 1640, 1610 cm$^{-1}$.

UV (MeOH: H$_2$O=1:1) λmax 234 nm (ε23,000), 290 (ε17,200), 470 nm (ε7,700).

MS (FAB): m/z 838 (M+H-HCO$_2$H)$^+$; high resolution mass spectrum calcd. for C$_{40}$H$_{44}$N$_3$O$_{17}$ (M+H)$^+$ 838.2671, found 838.2659.

$^1$H NMR (300 MHz, DMSO-d$_6$) δ(ppm): 0.91, 1.15 (3H, 2d, J=6 Hz, 5'-Me), 1.34 (3H, d, J=7 Hz, 17-Me), 2.28, 2.29 (3H, 2s, 3-Me), 3.11, 3.21 (3H, 2s, NMe), 3.0-4.0 (m), 3.91 (3H, s, 11-OMe), 4.3-4.7 (5-H, m, 17-H, CHCO, 5-H, 6-H, 1'-H), 5.7 (3H, br), 6.72 (1H, s, 10-H), 6.84 (1H, s, 4-H), 7.13 (1H, d, J=2.2 Hz, 12-H), 7.75 (1H, s, 7-H), 8.13 (1H, s, HCO$_2$), 8.78, 8.85 (2H, d, J=7 Hz, 16-H), 13.17 (br).

N-t-Boc-(L)-glutamic acid δ-benzyl α-N-hydroxysuccinimide ester was prepared according to the following procedure.

To a stirred mixture of N-t-Boc-(L)-glutamic acid δ-benzyl ester (10.12 g, 30 mmol; Vega Chemical) and N-hydroxysuccinimide (4.30 g, 33 mmol; Aldrich) in CH$_2$Cl$_2$ (200 ml) was added N,N'-dicyclohexylcarbodiimide (6.81 g, 33 mmol; E. Merck). The mixture was heated at reflux for 10 minutes and then stirred at room temperature for 5 hours. The precipitate was removed and washed with CH$_2$Cl$_2$. The filtrate and washing were combined and evaporated in vacuo to dryness. The residual oil was triturated with hexane and then with n-pentane. The semi-solid was dissolved in Et$_2$O (300 ml), removing the insoluble by filtration. The filtrate was concentrated in vacuo to dryness, giving 11.8 g (27.2 mmol, yield 90.6%) of the title compound as off-white foam.

$^1$H NMR (300 MHz, DMSO-d$_6$) δ(ppm): 1.44 (9H, s, t-Bu), 2.05 (1H, m, 3-H), 2.17 (1H, m, 3-He), 2.64 (2H, s, succ-CH$_2$), 2.65 (1H, m, 4-H), 2.86 (3H, brs, succ-CH$_2$, 4-H), 4.50 (1H, dd, J=8, 13 Hz, 2-H), 5.16 (2H, s, CH$_2$Ar), 7.41 (5H, s, ArHs), 7.73 (1H, d, J=8 Hz, NH).

EXAMPLE 21. Preparation of N-(Allyl) pradimicin B (II, R$^1$=CH$_3$, R$^2$=H, R$^3$=CH$_3$, R$^4$=-CH$_2$CH=CH$_2$)

To a stirred suspension of pradimicin B (100 mg, 0.15 mmol; 85% pure by HPLC) in 1,2-dichloroethane (4 ml) was injected BSA (0.60 ml, 2.42 mmol), and the mixture was stirred at 70° C. under a dry nitrogen atmosphere for 2 hours. To the resulting dark brown solution was injected allyl iodide (0.088 ml, 0.94 mmol), and the mixture was stirred at 100° C. under a dry nitrogen atmosphere for 2.5 hours by which time HPLC indicated the reaction was complete. After cooling, the mixture was concentrated in vacuo, the residue dissolved in methanol (10 ml) and treated with 1N HCl (2 ml), and they quickly concentrated in vacuo to remove the methanol. The residue, diluted with H$_2$O was purified by column chromatography (reverse phase silica gel, Lichroprep RP-18, EM Science) eluting with H$_2$O and then with 40% CH$_3$CN/H$_2$O to obtain 37 mg (0.05 mmol, yield 35%) of the title compound as dark orange powder: Rt 4.95 minutes (purity 96%; HPLC, column: Microsorb Short One C$_{18}$, eluent: 50% CH$_3$CN/0.15% potassium phosphate buffer, pH 3.5, flow rate 1.2 ml/minute).

IR (KBr) γmax: 3390, 2927, 1731, 1606 cm$^{-1}$.

UV (MeOH: H$_2$O=1:1) λmax: 234 (ε21,700), 286 (ε17,600), 480 nm (ε7,600).

MS (FAB): m/z 749 (M+H)$^+$.

$^1$H NMR (300 MHz, DMSO-d$_6$) δ(ppm): 1.25 (3H, d, J=7.2 Hz, 5'-Me), 1.31 (3H, d, J=7.3 Hz, 17-Me), 2.27 (3H, s, 3-Me), 2.83 (3H, brs, NMe), 3.2-3.9 (m, 2'-H, 3'H, 4'H, 5'-H), 3.93 (3H, brs, 11-OMe), 4.35-4.49 (3H, m, 5-H, 6-H, 17-H), 4.67 (1H, d, 1'-H), 5.50-5.57 (2H, m, H$_2$C=), 5.55-5.64 (1H, m, =CH), 5.80-5.95 (2H, brs, D$_2$O exchangeable), 6.1-6.2 (2H, brs, D$_2$O exchangeable), 6.89 (1H, d, J=2 Hz, 10-H), 7.02 (1H, s, 4-H), 7.25 (1H, d, J=2 Hz, 12-H), 8.01 (1H, s, 7-H), 8.58 (1H, d, J=6.9 Hz, CONH, D$_2$O exchangeable ), 12.88 (1H, s, D$_2$O exchangeable).

EXAMPLE 22. Preparation of N-(Allyl) pradimicin A (II, R$^1$=CH$_3$, R$^2$=β-D-xylosyl, R$^3$=CH$_3$, R$^4$=-CH$_2$CH=CH$_2$)

To a suspension of pradimicin A HCl (50 mg, 0.057 mmol) in 1,2-dichloroethane (2 ml) was injected BSA (0.25 ml, 1.01 mmol), and the mixture was heated at 40° C. under a dry nitrogen atmosphere for 1 hour by which time most of pradimicin A went into solution. To this solution was added allyl iodide (40 μl, 0.44 mmol), and the mixture was stirred at refluxing temperature for 11 hours. After cooling, the mixture was concentrated in vacuo, and the residue, dissolved in MeOH (5 ml), was treated with 1N HCl (1 ml). The mixture was concentrated in vacuo, and the residue was desalted by HP-20 column eluting first with H₂O and then with 80% (V/V) acetone/H₂O (pH 3) to obtain 42 mg (0.048 mmol, yield 85%) of the title compound as reddish powder: Rt 3.10 minutes (purity 93%; HPLC, column: Microsorb Short One $C_{18}$, 4.6 mm I.D.×100 μm, 3 μm, Rainin Instrument Co., eluent: 50% buffer (0.15% KH₂PO₄, pH 3.5)/CH₃CN, flow rate: 1.2 ml/minute, detection: UV absorption at 254 nm).

IR (KBr) γmax: 3400, 1730, 1630 (sh), 1610 cm⁻¹.

UV (MeOH: H₂O=1:1) λmax: 234 (ε29,000), 288 (ε23,000), 476 (ε9,850).

MS (FAB): m/z 881 (M+H)⁺; HRMS; calcd. for $C_{43}H_{49}N_2O_{18}$ (M+H)⁺ 881.1980, found 881.2960.

¹H NMR (300 MHz, DMSO-d₆) δ(ppm): 1.32 (3H, brm, 5'-Me), 1.32 (3H, d, J=7.3 MHz, 17-Me), 2.28 (3H, s, 3-Me), 2.66 (3H, br, NMe), 3.0–3.2 (3H, m, 5''-H, 2''-H, 3''-H), 3.71 (1H, dd, J=11 Hz, 5 Hz, 5''-H), 3.95 (3H, s, 11-OMe), 4.3–4.7 (5H, m, 17-H, 1''-H, 5-H, 6-H, 1'-H), 5.1 (2H, m, =CH₂), 5.8 (1H, m, CH=) 6.93 (1H, d, 10-H), 7.04 (1H, s, 4-H), 7.28 (1H, d, J=2 Hz, 12-H), 8.04 (1H, s, 7-H), 8.57 (1H, d, J=6.9 Hz, CONH, exchanged with D₂O), 12.88 (1H, s, exchanged with D₂O).

EXAMPLE 23. Preparation of N-(Propargyl) pradimicin B (II, R¹=CH₃, R²=H, R³=CH₃, R⁴=-CH₂C≡CH)

To a suspension of pradimicin B (100 mg, 0.14 mmol; 85% pure by HPLC) in 1,2-dichloroethane (5 ml) was injected BSA (0.6 ml, 2.4 mmol), and the mixture was stirred at 70° C. under a nitrogen atmosphere for 1.5 hours. To this was injected propargyl bromide (0.11 ml, 0.98 mmol, 80 wt % solution in toluene), and the mixture was stirred at 90° C. for 6 hours. The reaction mixture was concentrated in vacuo, and the residue, dissolved in methanol (10 ml), was mixed with 1N NaOH. The precipitate formed was collected and purified by column chromatography (reverse phase silica gel, Lichroprep, RP-18 EM Science) eluting with 70% MeOH/H₂O to obtain 31 mg (0.033 mmol, yield 23%) of the title compound as orange powder: Rt 4.05 minutes (purity 83%; HPLC, conditions: the same as given in Example 21.

IR (KBr) γmax: 3851, 3417, 2921, 2132, 1728, 1608 cm⁻¹.

UV (MeOH: H₂O=1:1) λmax: 232 (ε26,200), 288 (ε21,600), 474 (ε9,050).

MS (FAB): m/z 747 (M+H)⁺.

¹H NMR (300 MHz, DMSO-d₆) δ(ppm): 1.10 (3H, d, J=6.2 Hz, 5'-Me), 1.31 (3H, d, J=6.1 MHz, 17-Me), 2.28 (3H, s, 3-Me), 2.67 (3H, s, NMe), 2.88 (1H, br, HCC-), 3.07 (1H, br, 4'-H), 3.32 (s, D₂O exchangeable), 3.7 (4H, brs), 3.94 (3H, s, 11-OMe), 4.38–4.58 (4H, m) 6.08 (1H, br, D₂O exchangeable), 6.9 (1H, d, J=2 Hz, 10-H), 7.05 (1H, s, 4-H) 7.25 (1H, d, J=2 Hz, 12-H), 8.0 (1H, s, 7-H), 8.6 (1H, d, J=7 Hz, CONH, D₂O exchangeable), 12.91 (1H, s, D₂O exchangeable).

EXAMPLE 24. Preparation of N-(Benzyl) pradimicin A (II, R¹=CH₃, R²=β-D-xylosyl, R³=CH₃, R⁴=-CH₂Ph)

To a suspension of pradimicin A HCl (80 mg, 0.095 mmol; in 1,2-dichloroethane (6 ml) was injected BSA (0.6 ml, 2.42 mmol), and the mixture was heated at 70° C. under a dry nitrogen atmosphere for 1.5 hours. To this solution was injected benzyl bromide (83 μl, 0.70 mmol), and the mixture was stirred at 70° C. for 17 hours. After cooling, the mixture was concentrated in vacuo, and the residue, dissolved in MeOH (8 ml), was treated with 1N HCl (0.8 ml). The mixture was concentrated in vacuo, and the residue purified by column chromatography (reverse phase silica gel, Lichroprep RP-18, EM Science) eluting with H₂O, CH₃CN, and then MeOH. The MeOH fractions were concentrated in vacuo to obtain 37 mg (0.04 mmol, yield 42%) of the title compound as brown powder: Rt 4.40 minutes (purity 91%; HPLC, eluent: 50% buffer (0.15% KH₂PO₄, pH 3.5)/CH₃CN, other conditions: the same as given in Example 22.

IR (KBr) γmax: 3400, 1740, 1630 (sh), 1610 cm⁻¹.

UV (MeOH: H₂O=1:1) λmax: 232 (ε26,000), 284 (ε20,900), 480 (ε9,860).

MS (FAB): m/z 932 (M+2H)⁺; HRMS; calcd. for $C_{47}H_{51}N_2O_{18}$ (M+H)⁺ 931.3137, found 931.3116.

¹H NMR (300 MHz, DMSO-d₆) δ(ppm): 1.16 (3H, d, J=6.2 Hz, 5'-Me), 1.30 (3H, d, J=7.3 Hz, 17-Me), 2.17 (3H, s, 3-Me), 2.52 (3H, s, NMe), 2.9–3.2 (m), 3.71 (m), 3.92 (3H, s, 11-OMe), 4.00 (2H, s, CH₂Ph), 4.3–4.5 (4H, m, 17-H, 1''-H, 5-H, 6-H), 4.60 (1H, d, J=6 Hz, 1'-H), 6.85 (1H, s, 10-H), 6.97 ) (1H, s, 4-H), 7.22 (1H, s, 12-H), 7.2–7.4 (5H, m, ArHs), 7.94 (1H, s, 7-H), 8.59 (1H, d, J=7 Hz, CONH), 12.97 (1H, s).

What is claimed is:

1. A compound having the formula:

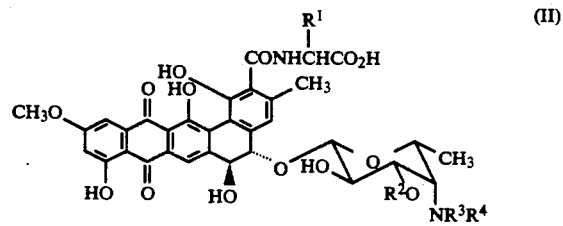

wherein R¹ is selected from the group consisting of H, methyl, and hydroxymethyl, and when R¹ is methyl or hydroxymethyl, the resulting amino acid has the D-configuration;

R² is H or β-D-xylosyl;

R³ is H or methyl; and

R⁴ is selected from the group consisting of $(C_{2-5})$alkenyl; $(C_{2-5})$alkynyl; substituted $(C_{1-5})$ alkyl; substituted $(C_{2-5})$ alkenyl; wherein the substituent for both the alkyl and alkenyl is a group selected from the group consisting of carboxy, $(C_{1-5})$alkoxycarbonyl, carbamyl, $(C_{1-5})$alkylcarbamyl, di$(C_{1-5})$alkylcarbamyl, and sulfonyl; $(C_{1-5})$alkanoyl substituted with a group selected from the group consisting of amino, $(C_{1-5})$alkylamino, and di$(C_{1-5})$alkylamino; L-glutamyl; formyl; benzyl; and p-tolysulfonylcarbamyl; or a pharmaceutically acceptable salt thereof.

2. A compound of claim 1 wherein R⁴ is $(C_{1-5})$alkyl substituted with a group selected from the group consisting of carboxy, $(C_{1-5})$alkoxycarbonyl, carbamyl, $(C_{1-5})$alkylcarbamyl, di$(C_{1-5})$alkylcarbamyl, and sulfonyl; or a pharmaceutically acceptable salt thereof.

3. A compound of claim 1 wherein R⁴ is $(C_{3-5})$alkenyl substituted with a group selected from the group consisting of carboxy, $(C_{1-5})$alkoxycarbonyl, carbamyl, $(C_{1-5})$alkylcarbamyl, and di$(C_{1-5})$alkylcarbamyl; or a pharmaceutically acceptable salt thereof.

4. A compound of claim 1 wherein $R^4$ is $(C_{1-5})$alkanoyl substituted with a group selected from the group consisting of amino, $(C_{1-5})$alkylamino, and di$(C_{1-5})$alkylamino; or a pharmaceutically acceptable salt thereof.

5. A compound of claim 1 wherein $R^4$ is selected from the group consisting of L-glutamyl, formyl, and p-tolysulfonylcarbamyl; or a pharmaceutically acceptable salt thereof.

6. A compound of claim 1 wherein $R^4$ is selected from the group consisting of benzyl, $(C_{3-5})$alkenyl, and $(C_{3-5})$alkynyl; or a pharmaceutically acceptable salt thereof.

7. A compound of claim 3 wherein $R^4$ is $(C_{3-5})$alkenyl substituted with a group selected from the group consisting of carboxy, and $(C_{1-5})$alkoxycarbonyl; or a pharmaceutically acceptable salt thereof.

8. A compound of claim 2 wherein $R^4$ is selected from the group consisting of carboxymethyl, carbamylmethyl, $(C_{1-5})$alkoxycarbonylmethyl, and sulfonylmethyl; or a pharmaceutically acceptable salt thereof.

9. A compound of claim 7 wherein $R^4$ is selected from the group consisting of 3-carboxy-2-propenyl and 3-$(C_{1-5})$alkoxycarbonyl-2-propenyl; or a pharmaceutically acceptable salt thereof.

10. A compound of claim 4 wherein $R^4$ $(C_{2-3})$alkanoyl substituted with a group selected from the group consisting of amino, $(C_{1-5})$alkylamino, and di$(C_{1-5})$alkylamino; or a pharmaceutically acceptable salt thereof.

11. A compound of claim 4 wherein $R^4$ is selected from the group consisting of glycyl, N,N-dimethylglycyl, and β-alanyl; or a pharmaceutically acceptable salt thereof.

12. A pharmaceutical composition which comprises an antifungal effective amount of a compound of claim 1 and a pharmaceutically acceptable carrier.

13. A method for treating fungal infections which comprises administering to a host in need of such treatment an antifungal effective dose of a compound of claim 1.

* * * * *